US008217141B2

(12) United States Patent
Skubatch

(10) Patent No.: US 8,217,141 B2
(45) Date of Patent: Jul. 10, 2012

(54) CRYSTALLINE AND AMORPHOUS FORMS OF PEPTIDE

(75) Inventor: Hanna Skubatch, Seattle, WA (US)

(73) Assignee: Neopro Labs, LLC, Seattle, WA (US)

( * ) Notice: Subject to any disclaimer, the term of this patent is extended or adjusted under 35 U.S.C. 154(b) by 888 days.

(21) Appl. No.: 12/154,076

(22) Filed: May 19, 2008

(65) Prior Publication Data

US 2009/0170784 A1 Jul. 2, 2009

Related U.S. Application Data

(60) Provisional application No. 60/950,552, filed on Jul. 18, 2007, provisional application No. 60/938,646, filed on May 17, 2007.

(51) Int. Cl.
*A61K 38/06* (2006.01)
(52) U.S. Cl. .................. 530/330; 514/18.3; 514/21.9
(58) Field of Classification Search .................. None
See application file for complete search history.

(56) References Cited

U.S. PATENT DOCUMENTS

| | | | |
|---|---|---|---|
| 5,189,064 A | 2/1993 | Blum et al. |
| 5,328,836 A | 7/1994 | Shima et al. |
| 5,492,894 A | 2/1996 | Bascom et al. |
| 5,506,202 A | 4/1996 | Vertesy et al. |
| 5,705,621 A | 1/1998 | Ravikumar |
| 5,760,044 A | 6/1998 | Archer |
| 5,854,226 A | 12/1998 | Penkler et al. |
| 6,419,931 B1 | 7/2002 | Vitiello et al. |
| 6,689,363 B1 | 2/2004 | Sette et al. |
| 6,794,144 B1 | 9/2004 | Saksela et al. |
| 6,849,714 B1 | 2/2005 | Bridon et al. |
| 7,244,599 B2 | 7/2007 | Tanner et al. |
| 7,557,088 B2 | 7/2009 | Skubatch |
| 2004/0254343 A1 | 12/2004 | Miyakaki et al. |
| 2006/0154863 A1 | 7/2006 | Skubatch |
| 2007/0185029 A1 | 8/2007 | Skubatch |
| 2007/0254811 A1 | 11/2007 | Skubatch |
| 2007/0259818 A1 | 11/2007 | Skubatch |
| 2009/0069237 A1 | 3/2009 | Skubatch |
| 2010/0137227 A1 | 6/2010 | Skubatch |

FOREIGN PATENT DOCUMENTS

| | | |
|---|---|---|
| DE | 4433564 A1 | 4/1996 |
| EP | 0514268 A1 | 11/1992 |
| EP | 0966975 A2 | 12/1999 |
| EP | 0966975 A3 | 4/2002 |
| EP | 0966975 B1 | 9/2005 |
| JP | 6-107683 A | 4/1994 |
| WO | WO 97/44447 A2 | 11/1997 |
| WO | WO 97/44447 A3 | 3/1998 |
| WO | WO 00/54805 A1 | 9/2000 |
| WO | WO 00/69900 A2 | 11/2000 |
| WO | WO 00/69900 A3 | 2/2001 |
| WO | WO 01/82914 A2 | 11/2001 |
| WO | WO 02/19986 A1 | 3/2002 |
| WO | WO 00/69900 A3 | 7/2002 |
| WO | WO 01/82914 A3 | 8/2002 |
| WO | WO 02/060432 A1 | 8/2002 |
| WO | WO 02/066625 A1 | 8/2002 |
| WO | WO 03/006654 A2 | 1/2003 |
| WO | WO 03/006654 A3 | 10/2003 |
| WO | WO 2004/054614 A1 | 7/2004 |
| WO | WO 2004/058804 A1 | 7/2004 |
| WO | WO 2004/098644 A1 | 11/2004 |
| WO | WO 2004/099135 A2 | 11/2004 |
| WO | WO 2004/101797 A1 | 11/2004 |
| WO | WO 2004/099135 A3 | 2/2005 |
| WO | WO 2006/000034 A1 | 1/2006 |
| WO | WO 2006/006172 A2 | 1/2006 |
| WO | WO 2006/006172 A3 | 5/2006 |
| WO | WO 2006/045313 A2 | 5/2006 |
| WO | WO 2006/045314 A2 | 5/2006 |
| WO | WO 2006/045319 A2 | 5/2006 |
| WO | WO 2006/068768 A2 | 6/2006 |
| WO | WO 2006/045313 A3 | 8/2006 |
| WO | WO 2006/045319 A3 | 9/2006 |
| WO | WO 2006/045314 A3 | 4/2007 |
| WO | WO 2006/068768 A3 | 1/2008 |

OTHER PUBLICATIONS

Benvenuti et al. "Crystallization of soluble proteins in vapor diffusion for x-ray crystallography," Nature Protocols, 2007, vol. 2. No. 2, 1633-1651.*
Cudney "Protein Crystallization and Dumb Luck" The Rigaku Journal 1999, vol. 16. No. 1, 1-7.*
Drenth "Crystallizing a Protein" in Principles of Protein X-Ray Crystallography,1999, 2$^{nd}$ Edition, pp. 1-22.*
Kundrot "Which strategy for a protein crystallization project?" CMLS, Cell. Mol. Life Sci., 2004, vol. 61, 525-536.*
McPherson "Current Approaches to Macromolecular Crystallization," Eur. J. Biochem, 1990, vol. 189, 1-23.*
Singhai et al. "Drug polymorphism and dosage form design: a practical perspective" Advanced Drug Delivery Reviews, 2004, 56, 335-347.*
Byrn et al. "Chemical reactivity in solid-state pharmaceuticals: formulation implications," Advanced Drug Delivery Reviews, 2001, 48, 115-136.*
Bis et al. "Defining & Addressing Solid-State Risks After the Proof-of-Concept Stage of Pharmaceutical Development," Drug Development & Delivery, Apr. 2011, pp. 32-34.*
U.S. Appl. No. 13/012,608, filed Jan. 24, 2011, Skubatch.
Office action dated Feb. 28, 2010 for AU Application No. 2005319578.
Shi, et al. Therapeutic polypeptides based on HBcAg(18-27) CTL epitope can induce antigen-specific CD(8)(+) CTL-mediated cytotoxicity in HLA-A2 transgenic mice. World J Gastroenterol. Apr. 15, 2004;10(8):1222-6.
Gimbel, et al. The efficacy and safety of oral immediate-release oxymorphone for postsurgical pain. Anesth Analg. Nov. 2004;99(5):1472-7.
International search report dated Oct. 29, 2008 for PCT Application No. US2008/064171.

(Continued)

*Primary Examiner* — Christina Bradley
(74) *Attorney, Agent, or Firm* — Wilson Sonsini Goodrich & Rosati

(57) ABSTRACT

The present invention relates to the crystalline and amorphous structures of SEQ ID NO:1 (FLPS), methods of making the same and use in treatment of various diseases and conditions.

2 Claims, 8 Drawing Sheets

OTHER PUBLICATIONS

International search report dated Nov. 13, 2007 for PCT Application No. US2005/42682.

International search report dated Feb. 10, 2009 for PCT Application No. US2008/70534.

International search report dated Sep. 29, 2008 for PCT Application No. US2007/65404.

Keinath, et al. Evaluation of biological and chemical seed treatments to improve stand of snap bean across the southern United States. Crop Protection. 2000; 19(7):501-509.

Kiyatkin, et al. Brain and body hyperthermia associated with heroin self-administration in rats. J Neurosci. Feb. 1, 2002;22(3):1072-80.

Larkindale, et al. Protection against Heat Stress-Induced Oxidative Damage in *Arabidopsis* Involves Calcium, Abscisic Acid, Ethylene, and Salicylic Acid. Plant Physiol, Feb. 2002, vol. 128, pp. 682-695.

Lufty, et al. Orphanin FQ/nociceptin blocks cocaine-induced behavioral sensitization in rats. Psychopharmacology (Berl). Nov. 2002;164(2):168-76.

Moore, et al. The efficacy of locally applied morphine in post-operative pain after bilateral third molar surgery. Br J Clin Pharmacol. Mar. 1994;37(3):227-30.

Reimer-Kent, J. From theory to practice: preventing pain after cardiac surgery. Am J Crit Care. Mar. 2003;12(2):136-43.

Syamsuwida, et al. Time and method of floral initiation and effect of paclobutrazol on flower and fruit development in *Shorea stenoptera* (Dipterocarpaceae). Tree Physiol. Apr. 1997;17(4):211-9.

Unlugenc, et al. Pre-emptive analgesic efficacy of tramadol compared with morphine after major abdominal surgery. Br J Anaesth. Aug. 2003;91(2):209-13.

Weiss, et al. A tricyclic ring system replaces the variable regions of peptides presented by three alleles of human MHC class I molecules. Chem Biol. Jun. 1995;2(6):401-7.

Bertoletti, et al. Definition of a minimal optimal cytotoxic T-cell epitope within the hepatitis B virus nucleocapsid protein. J Virol. 1993; 67(4):2376-80.

Chen, et al. Epsin is an EH-domain-binding protein implicated in clathrin-mediated endocytosis. Nature. 1998; 394:793-7.

Dinkova-Kostova, A., et al. (+)-Pinoresinol/(+)-Lariciresinol Reductase from *Forsythia* Intermedia. J. Biol. Chem. 1996; 271(46):29473-82.

Fujita, et al. Recombinant pinoresinol-lariciresinol reductases from western red cedar (*Thuja plicata*) catalyze opposite enantiospecific conversions. J. Biol. Chem. 1999; 274(2):618-27.

Gang, D. et al. Evolution of Plant Defense Mechanism. J. Biol. Chem. 1999; 274(11):7516-7527.

Hawks, et al. Opioid Peptides. Drug Abuse Research Monograph. # 70, 1986.

Horikawa, et al. Isolation and structural organization of the human preproenkephalin B gene. Nature. 1983; 306:611-4.

Latvala-Kilby, et al. The complete nucleotide sequence of RNA2 of blackcurrant reversion nepovirus. Virus Research. 1999; 65:87-92.

Lers, et al. The expression of a grapefruit gene encoding an isoflavone reductase-like protein is induced in response to UV irradiation. Plant Mol. Biol. 1998; 36:847-56.

Messer, W. S. Vasopressin and Oxytocin. This page was last updated on Monday, Apr. 3, 2000. Available at http://www.neurosci.pharm. utoledo.edu/MBC3320/vasopressin.htm. Accessed Dec. 19, 2006.

NCBI Database Accession No. AAC50454, Feb. 28, 2006.

NCBI Database Accession No. AAD09329, Feb. 28, 2006.

NCBI Database Accession No. NP_001017915, Feb. 28, 2006.

NCBI Database Accession No. NP_005532, Feb. 28, 2006.

Shorter, et al. GRASP55, a second mammalian GRASP protein involved in the stacking of Golgi cisternae in a cell-free system. EMBO J. 1999; 18(18):4949-60.

Salzet, M. Neuroimmunology of opioids from invertebrates to human. Neuro Endocrinol Lett. Dec. 2001;22(6):467-74.

Hruby, et al. Conformation-activity relationships of opioid peptides with selective activities at opioid receptors. Biopolymers. 1999;51(6):391-410.

Hruby, et al. Design of novel peptide ligands which have opioid agonist activity and CCK antagonist activity for the treatment of pain. Life Sci. 2003; 73:699-704.

Catania, et al. Peptide modulation of fever and inflammation within the brain. Ann N Y Acad Sci. Sep. 29, 1998;856:62-8.

Emel'ianova, et al. Effect of dermorphin analogs on thermoregulation of rats under various thermal conditions. Biology Bulletin. 2002; 29(3):284-289. (Translated from Izv Akad Nauk Ser Biol. May-Jun. 2002;(3):348-54.).

European search report dated Jun. 7, 2010 for Application No. 5852156.8.

Kalliomaki, et al. Prolactin-releasing peptide affects pain, allodynia and autonomic reflexes through medullary mechanisms. Neuropharmacology. Mar. 2004;46(3):412-24.

Le Guen, et al. Pain management by a new series of dual inhibitors of enkephalin degrading enzymes: long lasting antinociceptive properties and potentiation by CCK2 antagonist or methadone. Pain. Jul. 2003;104(1-2):139-48.

Tatro, et al. The central melanocortin system and fever. Ann N Y Acad Sci. Jun. 2003;994:246-57.

Wollemann, et al. Non-opioid actions of opioid peptides. Life Sci. Jun. 4, 2004;75(3):257-70.

McPherson. A comparison of salts for the crystallization of macromolecules. Protein Sci. 2001; 10(2):418-22.

Pikal, et al. The stability of insulin in crystalline and amorphous solids: observation of greater stability for the amorphous form. Pharm Res. 1997; 14(10):1379-87.

Shenoy, et al. Stability of crystalline proteins. Biotechnol Bioeng. 2001; 73(5):358-69.

Office action dated Mar. 25, 2011 for JP Application No. 2007-543505. (in Japanese with English translation).

\* cited by examiner

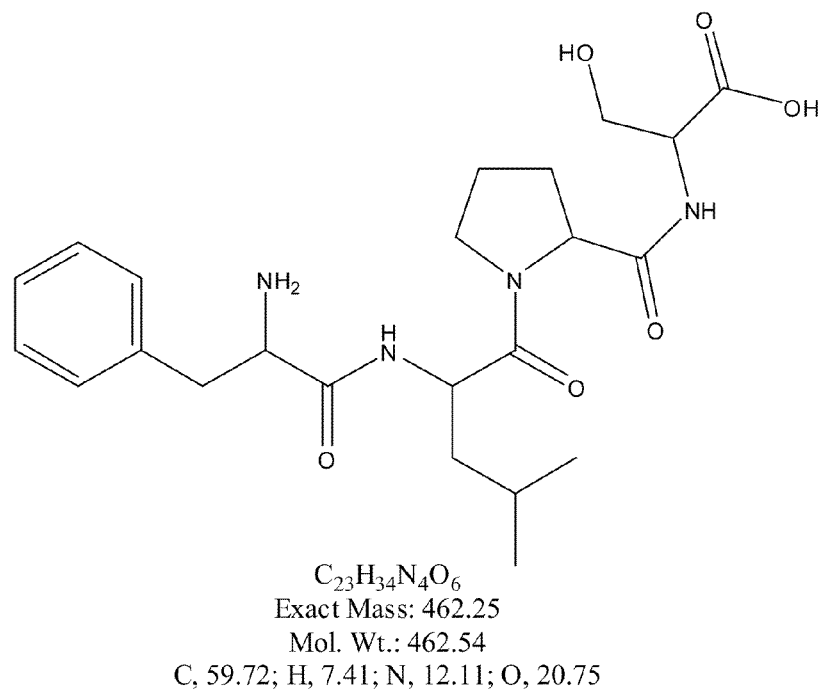
C₂₃H₃₄N₄O₆
Exact Mass: 462.25
Mol. Wt.: 462.54
C, 59.72; H, 7.41; N, 12.11; O, 20.75
Figure 1
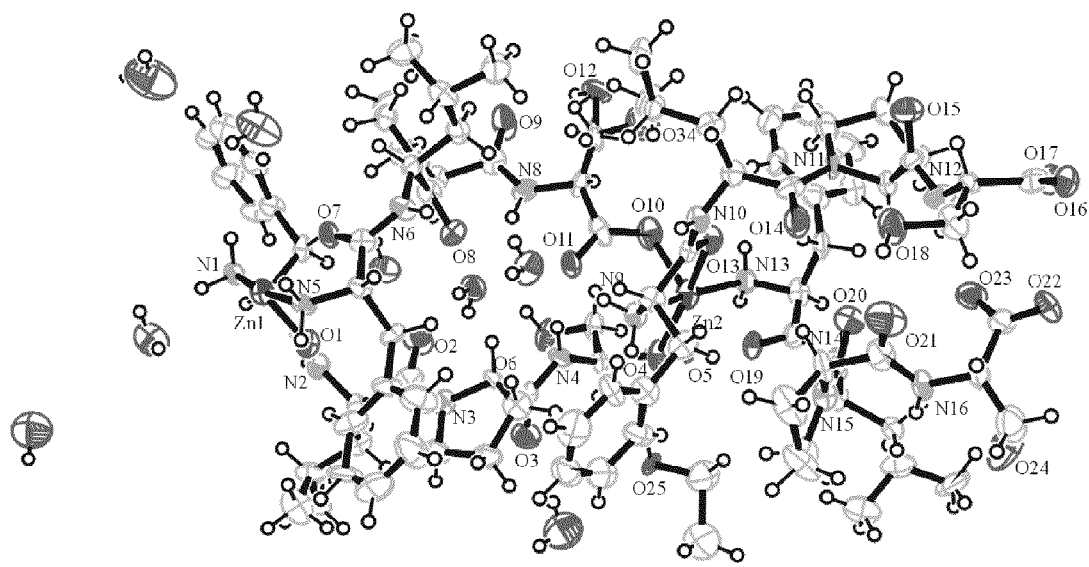
Figure 2. Depicted are 2 zinc ions (Zn1 and Zn2) in coordination with four SEQ ID NO:1

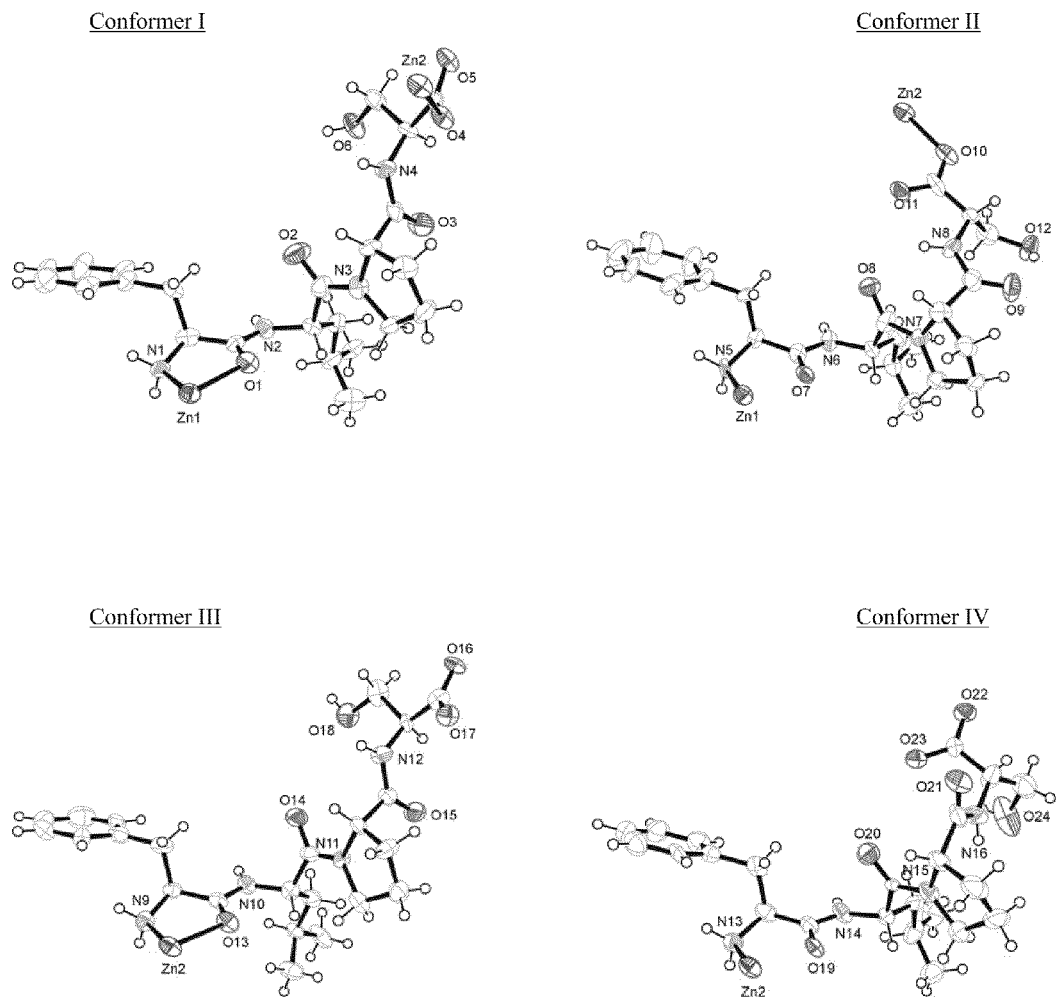
Figure 3. Conformers I and II show a $Zn^{2+}$ cation (Zn1) complexed to two SEQ ID NO:1. Conformers III and IV show a $Zn^{2+}$ cation (Zn2) complexed to two SEQ ID NO:1.

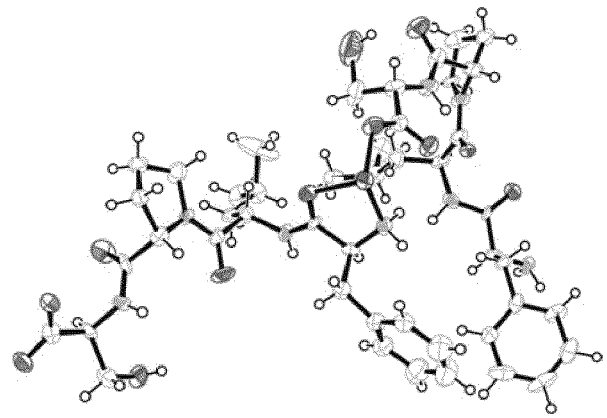
Figure 4. A $Zn^{2+}$ (center) ion is complexed to two SEQ ID NO:1
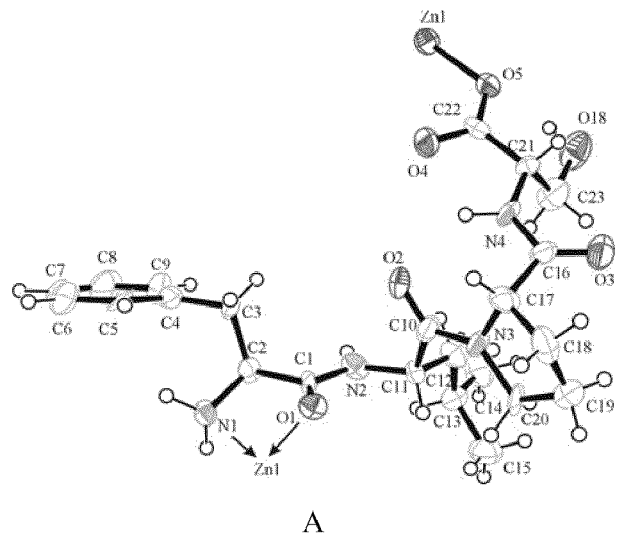
A
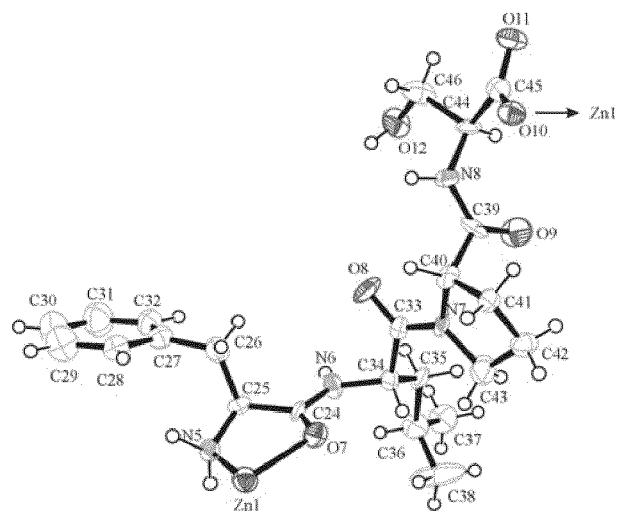
B
Figure 5. A and B show complexation of SEQ ID NO:1 with a $Zn^{2+}$ ion (Zn1)

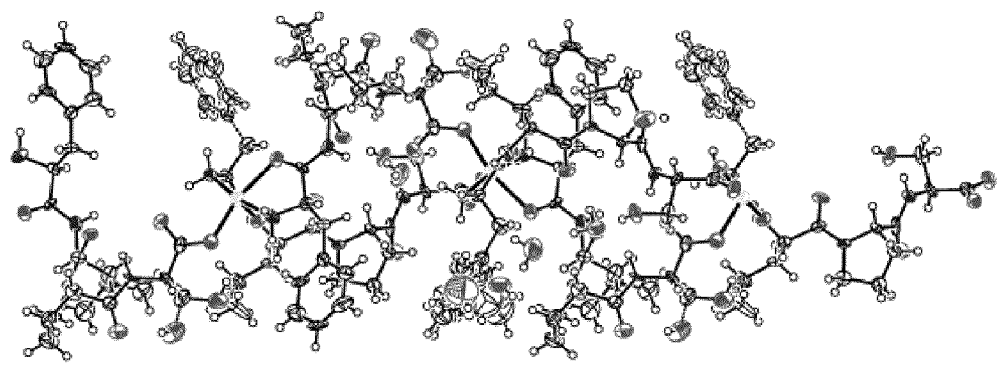
Figure 6. A plot generated by the cifcheck program shows $Zn^{2+}$ ions coordinated to SEQ ID NO:1 peptides thoughout the crystal.
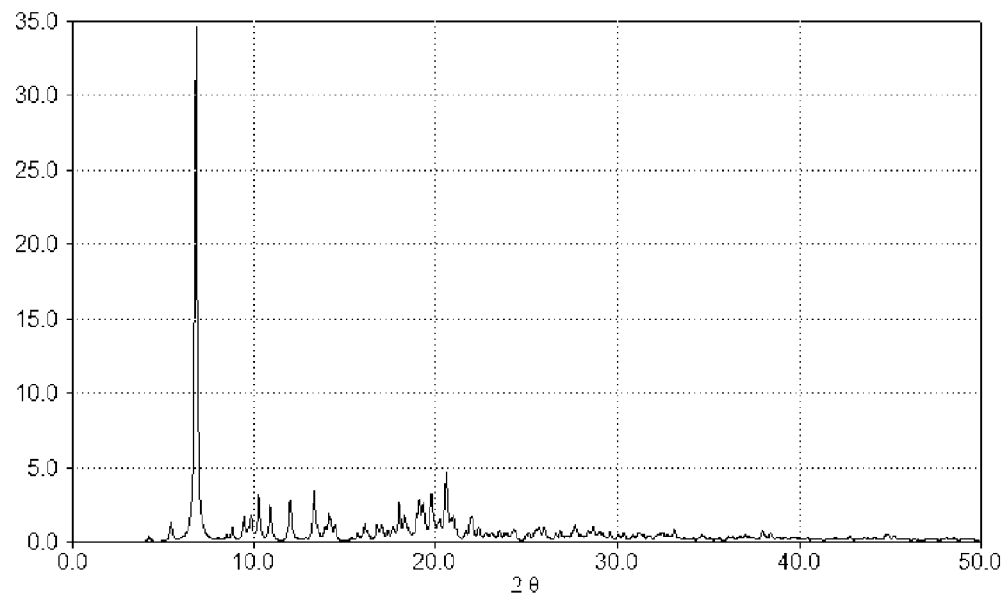
Figure 7

CRYSTALLINE AND AMORPHOUS FORMS OF PEPTIDE

CROSS-REFERENCE TO RELATED APPLICATIONS

This application claims the benefit of U.S. Provisional Application No. 60/950,552, entitled "Crystalline Pharmaceutical" filed on Jul. 18, 2007, and U.S. Provisional Application No. 60/938,646, entitled "Amorphous Form of Peptide" filed on May 17, 2007, the disclosures of which are hereby incorporated by reference in their entirety.

BACKGROUND OF THE INVENTION

A peptide comprising FLPS (SEQ ID No:1), has been shown to have utility for the treatment of metabolic and mitochondrial conditions, such as pain, temperature regulation (e.g., fever, Reynaud's syndrome), inflammation, neoplastic growth (e.g., cancer), innate immune response activation, and ability to fight parasites and pathogens, skin and dermatological conditions, diabetes related disorders, wound healing, undesirable drug side effects, and neurological and neurodegenerative conditions (e.g., Alzheimer's), learning, memory, anti-stress and anxiety.

To prepare pharmaceutical compositions containing the compounds described herein, such as for example, the 4-mer peptide having the SEQ ID No:1, for administration to mammals in accordance with the requirements of U.S. and international health registration authorities (e.g., FDA's Good Manufacturing Practices ("GMP")), it is desirable to have a compound described herein in a stable form, such as a stable crystalline form having constant physiochemical and biological properties. The forms of the present invention provide enhanced properties such as improved solubility and/or oral bioavailability.

Amorphous forms of peptides having a SEQ ID NO:1 are also disclosed herein, as are their processes for preparation. SEQ ID NO:1 and processes for its preparation and uses are further disclosed in U.S. application Ser. No. 11/287,157, filed Nov. 25, 2005, which is hereby incorporated herein by reference.

SUMMARY OF THE INVENTION

The present invention relates to crystalline and amorphous forms of a composition comprising, consisting essentially of, or consisting of SEQ ID NO: 1 (FLPS).

In one aspect, the invention involves compositions comprising, consisting essentially of, or consisting of a peptide comprising a SEQ ID NO:1 and a cation, such as for example $Zn^{2+}$ or $Mg^{2+}$. In another aspect, the invention contemplates a crystalline form of a peptide comprising, consisting essentially of, or consisting of a SEQ ID NO:1. In one embodiment, the crystalline form further comprises at least one cation such as, for example, $Ba^{2+}$, $Ca^{2+}$, $Cr^{2+}$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, or $Zn^{2+}$. In one embodiment, the crystalline form comprises one or more $Zn^{2+}$ cations. In a further embodiment, the crystalline form can be solvated with an organic solvent. Non-limited examples of organic solvents suitable for solvation include solvents such as methanol, ethanol, n-propanol, isopropanol, n-butanol, isobutanol, t-butanol, n-amyl alcohol, isoamyl alcohol, t-pentanol, ethyl acetate, acetone, tetrahydrofuran, chloroform, methylene chloride, propylene glycol, methylethyl ketone, and dimethylsulfoxide. In one embodiment, the organic solvent is ethanol. Also contemplated within the scope of the present invention is a crystalline form of a peptide comprising, consisting essentially of, or consisting of a SEQ ID NO:1 in a hydrated form. The hydrated form may further comprise an organic solvent such as by way of example only, ethanol. In a further embodiment, the crystalline form may exist in a desolvated state.

The invention herein also provides for a peptide complex comprising at least 2 peptides having a SEQ ID NO: 1. In one embodiment, the peptide complex herein comprises at least one cation. Examples of cations suitable for complexation with a peptide described herein can be, for example only, $Ba^{2+}$, $Ca^{2+}$, $Cr^{2+}$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, and $Zn^{2+}$. In another embodiment, the cation is $Zn^{2+}$ or $Mg^{2+}$. In another embodiment the peptide complex described herein comprises at least 4 peptides having a SEQ ID NO: 1. The peptide complexes presented herein are not limited to complexation with a single cation. It is contemplated that a peptide, such as for example only, a peptide comprising, consisting essentially of, or consisting of SEQ ID NO:1 can form a complex with at least 2 cations. In one embodiment, the peptide complex comprises at least 2 $Zn^{2+}$ cations.

In one aspect the invention provides a crystalline form of the peptide complex described herein.

In another aspect, the invention provides a unit cell comprising two peptide complexes described herein.

Described herein is an amorphous form of a peptide comprising, consisting essentially of, or consisting of a SEQ ID NO: 1. Amorphous forms presented herein can further comprise at least one cation. Cations suitable for amorphous forms may include cations such as $Ba^{2+}$, $Ca^{2+}$, $Cr^{2+}$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, and $Zn^{2+}$. In one embodiment, the amorphous form comprises a $Zn^{2+}$ or $Mg^{2+}$ cation.

The present invention also contemplates a pharmaceutical composition comprising a crystalline form of a peptide comprising a SEQ ID NO: 1 and a pharmaceutically acceptable excipient or binder.

In one aspect is a process for preparing a crystalline form of a peptide comprising, consisting essentially of, or consisting of a SEQ ID NO: 1, comprising the steps of:
(a) preparing a solution of the peptide comprising the SEQ ID NO: 1 in a solvent selected from: water, methanol, ethanol, 2-propanol, 2-butanol, ethyl acetate, dichloromethane, tetrahydrofuran, 1-butanol, acetone, acetonitrile, ethyl acetate, chloroform, toluene, hexane, water:toluene, water:toluene:chloroform, chloroform:methanol, toluene:methanol, isopropyl ether, pentane:ethanol, heptane:ethanol, and mixtures thereof; and
(b) recovering the crystalline form.

In another aspect, the present invention provides for a process for preparing an amorphous form of a peptide comprising a SEQ ID NO: 1 comprising the steps of:
(a) preparing a solution of the peptide having the SEQ ID NO: 1 in a solvent selected from: water, methanol, ethanol, 2-propanol, 2-butanol, ethyl acetate, dichloromethane, tetrahydrofuran, 1-butanol, acetone, acetonitrile, ethyl acetate, chloroform, toluene, hexane, water:toluene, water:toluene:chloroform, chloroform:methanol, toluene:methanol, isopropyl ether, pentane:ethanol, heptane:ethanol, and mixtures thereof; and
(b) recovering the amorphous form.

In one embodiment, the present invention provides for a process for preparing an amorphous form by slow or fast evaporation.

Also contemplated herein is a method of treating pain in a subject comprising administering to the subject a therapeutically effective amount of a crystalline or amorphous form of a peptide comprising, consisting essentially of, or consisting of a SEQ ID NO: 1.

The use of a crystalline or amorphous form of a peptide comprising, consisting essentially of, or consisting of a SEQ ID NO: 1 for the formulation of a medicament for the treatment of pain is also contemplated herein.

Also described herein are articles of manufacture comprising packaging material, pharmaceutical compositions presented herein which are effective for treating pain, within the packaging material and a label that indicates that the composition is used for the treatment of pain.

The compositions herein can be used to modulate, prevent, or treat pain, inflammation, infections (e.g., bacterial fingi, viruses, etc.), and metabolic processes or conditions in an organism. Examples of metabolic conditions include, but are not limited to, pain, wound healing, inflammation, heat production, fever, homeothermy, breakdown of triglycerides, glycolysis, Krebs cycle, fermentation, photosynthesis, metabolic rate, biotic and abiotic stress, secretions, oxidative stress, stress, neoplastic growth, skin condition, cardiovascular conditions, neurological and neurodegenerative conditions, mental and behavioral disorders. Such processes or conditions can occur in a cell, group of cells, or an entire organism.

The compositions herein can be used for modulating, preventing, treating condition(s) in organisms. Such organisms can be animals and/or plants.

The compositions herein (e.g., a crystalline or amorphous form comprising of, consisting essentially of, or consisting of a peptide having a SEQ ID NO:1) can be used to modulate or treat pain, such as nociceptive (non-chronic) pain, acute and chronic pain, neuropathic pain, idiopathic pain, headaches, low back pain, cancer pain, arthritis pain, sprains, bone fractures, pain resulting from burns, pain associated with bumps, pain associated with bruises, inflammatory pain (e.g., from an infection or arthritic disorder), pain from obstructions, myofascial pain, pain from nerve trauma (e.g., dystrophy/causalgia), phantom limb pain, entrapment neuropathy (e.g., carpal tunnel syndrome), and peripheral neuropathy.

Preferably, a composition comprising, consisting essentially of, or consisting of a crystalline or amorphous form of a peptide of SEQ ID NO:1 is administered to an animal to treat pain. Such pain can be acute and chronic pain, neuropathic pain, or idiopathic pain. It is further contemplated that compositions comprising a crystalline or amorphous form described herein (e.g., SEQ ID NO: 1) are co-administered with one or more other pain relief medications. For example, a crystalline or amorphous peptide form or a mixture thereof described herein, such as SEQ ID NO: 1 can be administered simultaneously with, co-formulated with, or administered in the same therapy as a pain reliever such as small molecules (e.g., non-narcotic and narcotic analgesics) and peptide opioids.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The patent or application file contains at least one drawing executed in color. Copies of this patent or application publication with color drawings will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates the 2D molecular structure of SEQ ID NO:1.

FIG. 2 illustrates an asymmetric unit of hydrated crystalline SEQ ID NO:1.

FIG. 3 illustrates four conformers of SEQ ID NO:1.

FIG. 4 illustrates SEQ ID NO:1 complex from an asymmetric unit.

FIG. 5 illustrates two individual peptides (A and B) from a crystalline SEQ ID NO:1 complex.

FIG. 6 illustrates a plot generated to show peptide arrangement throughout the crystal.

FIG. 7 illustrates a contemplated powder spectrum of hydrated crystal form of SEQ ID NO:1 calculated for Cu radiation.

DETAILED DESCRIPTION OF THE INVENTION

Figure 8:
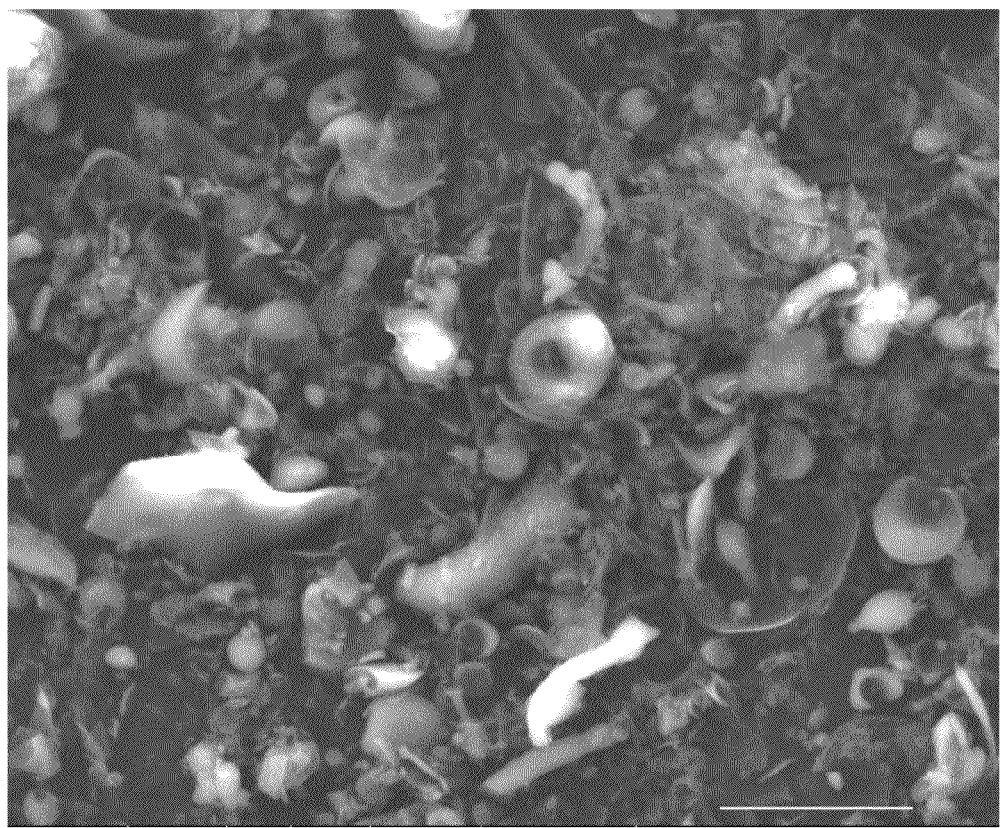
FIG. 8 illustrates scanning electron microscope of an amorphous SEQ ID NO:1.

The physical properties of a drug are important for obtaining maximum efficacy. For example, the rate of dissolution of an active ingredient in the stomach can have therapeutic consequences since it imposes an upper limit on the rate at which an orally administered active ingredient can reach the bloodstream. The rate of dissolution is also a consideration in formulating syrups, elixirs and other liquid medicaments. The solid-state form of a compound may also affect its behavior on compaction and its storage stability. Thus, it is important to control the conditions under which a drug is obtained in solid form.

Moreover, the physical characteristics of a compound are influenced by the conformation and orientation of molecules, which defines a particular crystallinic form of a compound. The crystallinic form may give rise to thermal behavior different from that of the amorphous material. Thermal behavior is measured in the laboratory by such techniques as capillary melting point, thermogravimetric analysis (TGA), and differential scanning calorimetry (DSC) and it can distinguish some crystallinic forms from others. A particular crystallinic form may also give rise to distinct spectroscopic properties that may be detectable by powder X-ray crystallography, $^{13}$C-NMR spectrometry, and infrared spectrometry.

The following terms as used herein have the meanings indicated.

As used in this specification, and in the appended claims, the singular forms "a", "an", "the", include plural references unless the context clearly dictates otherwise.

The terms "comprising" and "including" are used in an open, non-limiting sense.

The terms "pharmaceutically acceptable salt" is intended to mean a salt that retains the biological effectiveness of the free acids and bases of the specified compound and that is not biologically or otherwise undesirable.

When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include calcium, organic amino, zinc, magnesium, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science*, 66:1-19 (1977)).

In one aspect, the invention contemplates a salt comprising, consisting essentially of, or consisting of a peptide having a SEQ ID NO:1 (FLPS) and at least one cation. In one aspect, a cation is a 2+ cation such as any of the following: $Ba^{2+}$, $Ca^{2+}$, $Cr^{2+}$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, and $Zn^{2+}$. In one embodiment, the cation is $Zn^{2+}$. In another embodiment of the present invention, the cation is $Mg^{2+}$. In a further embodiment, the salt is a pharmaceutically acceptable salt.

In one embodiment, the present invention contemplates a salt comprising, consisting essentially of, or consisting of a peptide having a SEQ ID NO:1 and at least one or two cations. In yet a further embodiment, such salt comprises two $Zn^{2+}$ cations. At least one or two $Zn^{2+}$ cations can be electrostatically attracted to a nitrogen or oxygen atom of the peptide comprising, consisting essentially of, or consisting of a SEQ ID NO:1. The present invention contemplates a salt comprising, consisting essentially of, or consisting of a peptide having a SEQ ID NO:1 in a crystal lattice. In another embodiment, such salt contains an organic solvent in the crystal lattice. In a further embodiment, the present invention is directed to a salt comprising, consisting essentially of, or consisting of a peptide having a SEQ ID NO:1 in a desolvated form.

Provided herein is a peptide complex comprising, consisting essentially of, or consisting of at least two peptides comprising, consisting essentially of, or consisting of a SEQ ID NO:1. In alternative embodiments, such peptide complex further comprises at least one cation. Examples of interactions forming such a peptide complex include, hydrogen bonding, van der Waals forces, dipole-dipole forces and ionic bonding. Such interactions can be via intramolecular interactions.

The at least one cation can be a 2+ cation such as, for example, any one of the following: $Ba^{2+}$, $Ca^{2+}$, $Cr^{2+}$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, and $Zn^{2+}$. In one embodiment, the at least one cation can be $Mg^{2+}$ or $Zn^{2+}$.

In another aspect, the peptide complex of the present invention further comprises an alcohol and/or water. In one embodiment, the alcohol is EtOH. In another aspect, the peptide complex described herein further comprises at least ½ EtOH molecule, and a $H_2O$ molecule. In yet another aspect, the peptide complex comprises 4 peptides having a SEQ ID NO:1 and two $Zn^{2+}$ cations. Also described herein is a peptide complex comprising 4 peptides having a SEQ ID NO:1, two $Zn^{2+}$ cations, a molecule of EtOH and $8H_2O$ molecules. In another embodiment, the $Zn^{2+}$ cation has an octahedral coordination.

Crystalline Forms

The present invention relates to the crystal properties of SEQ ID NO:1 (FLPS). One of the most precise methods to determine the three-dimensional structure of a polypeptide employs X-ray crystallography (See, e.g., Van Holde, (1971) Physical Biochemistry, Prentice-Hall, N.J., pp. 221 39). This technique relies on the ability of crystalline lattices to diffract X-rays.

In one aspect, the present invention provides a crystalline form of a peptide comprising, consisting essentially of, or consisting of a SEQ ID NO:1.

In one embodiment, the present invention, provides a crystalline form of a peptide comprising, consisting essentially of, or consisting of a SEQ ID NO:1 and at least one cation. The present invention contemplates a crystalline form wherein the peptide:cation ratio can be 1:1, 1:2, 1:3, 1:4, 2:1, 3:1, 4:1, 5:1, or 6:1. Suitable cations can be any 2+ cations such as by way of example only $Ba^{2+}$, $Ca^{2+}$, $Cr^{2+}$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, and $Zn^{2+}$. In another embodiment of the present invention the at least one cation is $Mg^{2+}$ or $Zn^{2+}$.

Provided herein is a crystalline form of a salt comprising, consisting essentially of, or consisting of a peptide having a SEQ ID NO:1 and at least one cation selected from $Ba^{2+}$, $Ca^{2+}$, $Cr^+$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, and $Zn^{2+}$. In another embodiment of the present invention the at least one cation is $Mg^{2+}$ or $Zn^{2+}$. In a further embodiment, the crystalline form further comprises a solvent.

In one aspect, the present invention contemplates a composition comprising a crystalline form of a peptide comprising, consisting essentially of, or consisting of SEQ ID NO:1 in a solvated form.

In another aspect of the present invention is a crystalline form of a peptide comprising, consisting essentially of, or consisting of SEQ ID NO:1 and an organic solvent. The organic solvent can be any one or more of the following: acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. Preferably, the solvent is selected from ethyl acetate, isopropyl acetate, tert-butylmethylether, heptane, isopropanol, and ethanol or more preferably, ethanol.

Any of the solvated crystal compositions described herein can further comprise polar organic solvents. Examples of such relatively polar organic solvents include methanol, ethanol, n-propanol, isopropanol, n-butanol, iso-butanol, t-butanol, n-amyl alcohol, iso-amyl alcohol, t-pentanol, ethyl acetate, acetone, tetrahydrofuran, chloroform, methylene chloride, propylene glycol, methylethyl ketone, dimethylsulfoxide and the like.

Residual solvents in pharmaceuticals are organic volatile chemicals that are used or produced in the manufacture of drug substances or excipients, or in the preparation of drug products. The solvents are not completely removed by practical manufacturing techniques. Appropriate selection of the solvent for the synthesis of drug substance may enhance the yield, or determine characteristics such as crystal form, purity, and solubility. Therefore, the solvent may sometimes be a critical parameter in the synthetic process.

In another aspect, the present invention provides a crystalline form of a peptide comprising, consisting essentially of, or consisting of a SEQ ID NO:1 in a hydrated form. In another embodiment, the present invention provides a crystalline form of a peptide comprising, consisting essentially of, or consisting of a SEQ ID NO:1 comprising substantially the same X-ray diffraction pattern as shown in FIG. 1. FIG. 1 provides a contemplated powder spectrum of a hydrated crystal form of SEQ ID NO:1 which is calculated for Cu radiation. The crystalline form described herein can also have substantially the same 2θ peak between about 10° and 40°, preferably about 10°.

The present invention also contemplates a hydrated crystal form comprising, consisting essentially of, or consisting of SEQ ID NO:1. Such hydrated crystal forms can include at least 1 or 2 molecules of water per peptide comprising, consisting essentially of, or consisting of SEQ ID NO:1. Also contemplated herein are hydrated crystal forms which can include between 1 to about 20 molecules of water per peptide comprising, consisting essentially of, or consisting of SEQ ID NO:1. Alternatively, hydrated crystal forms can include between about 1 to about 20 molecules of peptide per molecule of water.

Hydrated crystal forms described herein can also include a solvent. Such solvents can be any one or more of the following: acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the hydrated crystal form comprises a peptide comprising, consisting essentially of, or consisting of SEQ ID NO: 1 and an organic solvent such as ethanol. Hydrated crystal forms can include between 1 to about 20 molecules of water and between 1 and about 20 molecules of solvent, such as, for example, ethanol per peptide comprising, consisting essentially of, or consisting of SEQ ID NO:1. Preferably, the hydrated crystal form comprises about at least 2 molecules of water, at least 1 molecule of ethanol per molecule of peptide comprising, consisting essentially of, or consisting of SEQ ID NO:1, or more preferably about 1.785 molecules of water and 0.215 molecules of alcohol per molecule of peptide comprising, consisting essentially of, or consisting of SEQ ID NO:1.

Another asymmetric unit of the crystal contemplated herein comprises at least eight molecules of SEQ ID NO:1 and a molecule of ethanol. For another type of asymmetric unit of the crystal there are 4 molecules of SEQ ID NO:1 and a molecule of ethanol. Further embodiments include an asymmetric unit of the crystal where there are at least 2, 3, 4, 5, 6, 7, or 8 molecules of SEQ ID NO:1 per molecule of ethanol. Other asymmetric units of the crystal described herein include a combination of at least 2, 3, 4, 5, 6, 7, 8, 9, or 10 molecules of a peptide comprising, consisting essentially of, or consisting of SEQ ID NO:1 and at least 1, 2, 3, 4, 5, 6, 7, 8, 9, or 10 molecules of an alcohol.

Further embodiments include an asymmetric unit of the crystal where there are at least 1, 2, 3, 4, 5, 6, 7, 8, 9 or 10 molecules of water, at least 1, 2, 3, 4, 5, 6, 7, 8, 9, or 10 molecules of alcohol per molecule of peptide comprising, consisting essentially of, or consisting of SEQ ID NO:1. Other asymmetric units of the crystal described herein include a combination of at least 1, 2, 3, 4, 5, 6, 7, 8, 9, or 10 molecules of a peptide comprising, consisting essentially of, or consisting of SEQ ID NO:1, at least 1, 2, 3, 4, 5, 6, 7, 8, 9, or 10 molecules of an alcohol, and at least 1, 2, 3, 4, 5, 6, 7, 8, 9, 10 and up to at least 20 molecules of water. For another type of asymmetric unit of the crystal there are two molecules of SEQ ID NO:1 and 1 molecule of ethanol and 4 molecules of water. A further type of asymmetric unit of the crystal comprise four molecules of SEQ ID NO:1, 2 Zn2+ cations, an ethanol molecule and 8 water molecules as depicted in FIG. 2. Further, two complexes fill the unit cell also depicted in FIG. 2.

In some aspects of the invention, the asymmetric unit comprises 2, 3, 4, or more peptides comprising, consisting essentially of, or consisting of SEQ ID NO:1 each in a different conformation.

Also contemplated herein are asymmetric units of a crystal wherein the alcohol to water concentration ratio is disordered at a % concentration of 10:90, 20:80, 30:70, 40:60, 50:50, 60:40, 70:30, 80:20, and 90:10. Preferably, the alcohol to water concentration is disordered at a concentration of 40% alcohol to 60% water, or more preferably 43% alcohol with water at 57%. Water content of the crystal form may vary within this range depending on the temperature and water content of the environment of the crystal form.

The hydrated crystal forms described herein can be prepared from solution in water or from solutions in mixtures of water and water miscible organic solvents. Examples of water miscible organic solvents include $C_1$-$C_4$ alcohols such as methanol and ethanol. In the mixtures of water and water miscible organic solvents, the amount of water can vary from about 10% by volume to about 90% by volume, preferably, from about 10% to about 60% by volume, or more preferably by about 10% to about 40% by volume.

In one aspect, the present invention provides a coordinated structure of a molecular weight 4288.17 Da, z=1, and of the sum formula $C_{186}H_{302}N_{32}O_{65}Zn_4$ and a second coordinated structure of a molecular weight 1072.56 Da, z=4, and of the sum formula $C_{46.86}H_{75.72}N_8O_{16}Zn$.

In some aspects, a crystalline salt of SEQ ID NO:1 comprises at least 1 or 2 molecules of $Zn^{2+}$ per molecule of peptide comprising, consisting essentially of, or consisting of SEQ ID NO:1.

In one example, a crystalline form of a complex of at least 4 peptides comprising, consisting essentially of, or consisting of SEQ ID NO:1. Optionally such complex further comprises at least 1 or 2 cations. In some cases at least 4 peptides form a complex as shown in FIG. 3. Examples of cations include 2+ cations such as by way of example only, $Mg^{2+}$ or $Zn^{2+}$.

The present invention provides at least one zinc-binding site in SEQ ID NO:1. More preferably 2-binding sites.

The metal coordinating group in the complex can be a nitrogen group, a carboxy group, or a hydroxyl group. Thus, the present invention provides a new zinc-binding motif that forms at least two intermolecular coordinate bonds to a zinc ion.

The present invention provides a crystalline form of a peptide comprising, consisting essentially of, or consisting of SEQ ID NO:1 characterized by an XRPD pattern shown in FIG. 1 or substantially similar to that of FIG. 1.

In one embodiment the crystalline form belongs to the space group $P2_1$ as shown in FIG. 2. In another embodiment, the crystalline form comprises unit cell dimensions of a=10.04 Å, b=25.946 Å, c=20.820 Å.

In a further embodiment, the crystalline form of a peptide comprising, consisting essentially of, or consisting of SEQ ID NO:1 belongs to the space group $P2_12_12$, as shown in FIG. 4. In a further embodiment, the crystalline form comprises unit cell dimensions of a=9.929 Å, b=20.406 Å, and c=25.827 Å.

In another aspect, the present invention provides a process for preparing crystalline SEQ ID NO:1 comprising the steps of crystallizing SEQ ID NO: 1 from a mixture of water and a solvent such as an alcohol. In one embodiment, the alcohol is EtOH.

In a further aspect, the present invention provides for a process for preparing a crystalline form of a peptide comprising a SEQ ID NO: 1, comprising the steps of:
a. preparing a solution of the peptide comprising, consisting essentially of, or consisting of SEQ ID NO: 1 in a solvent such as water, methanol, ethanol, 2-propanol, 2-butanol, ethyl acetate, dichloromethane, tetrahydrofuran, 1-butanol, acetone, acetonitrile, ethyl acetate, chloroform, toluene, hexane, water:toluene, water:toluene:chloroform, chloroform:methanol, toluene:methanol, isopropyl ether, pentane:ethanol, heptane:ethanol, or mixtures thereof; and
b. recovering the crystalline form.

Amorphous Forms

The term "amorphous" refers to a non-crystalline form of a compound. Typically, an amorphous solid lacks a long-range order of the positions of the atoms. Amorphous forms may be more soluble than the crystalline form. Therefore, different extents of drug absorption may result with consequent differences in the degree of pharmacologic activity obtained from each.

An amorphous form of a peptide comprising, consisting essentially of, or consisting of SEQ ID NO:1. In one embodiment disclosed herein the amorphous form further comprises at least one cation. Such cations can be any 2+ charged cation. Examples include $Ba^{2+}$, $Ca^{2+}$, $Cr^{2+}$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, and $Zn^{2+}$. In another embodiment of the present invention is an amorphous form of SEQ ID NO:1 with at least one cation such as by way of example only $Mg^{2+}$ or $Zn^{2+}$.

An amorphous form of a peptide comprising, consisting essentially of, or consisting of SEQ ID NO:1 can be a solvated form. The solvent can be an organic solvent. Suitable solvents for amorphous forms described herein include: acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran or preferably ethanol. Also contemplated herein are amorphous forms in a hydrated state. Such hydrated amorphous forms can further comprise an alcohol, preferably ethanol.

Figure 9:
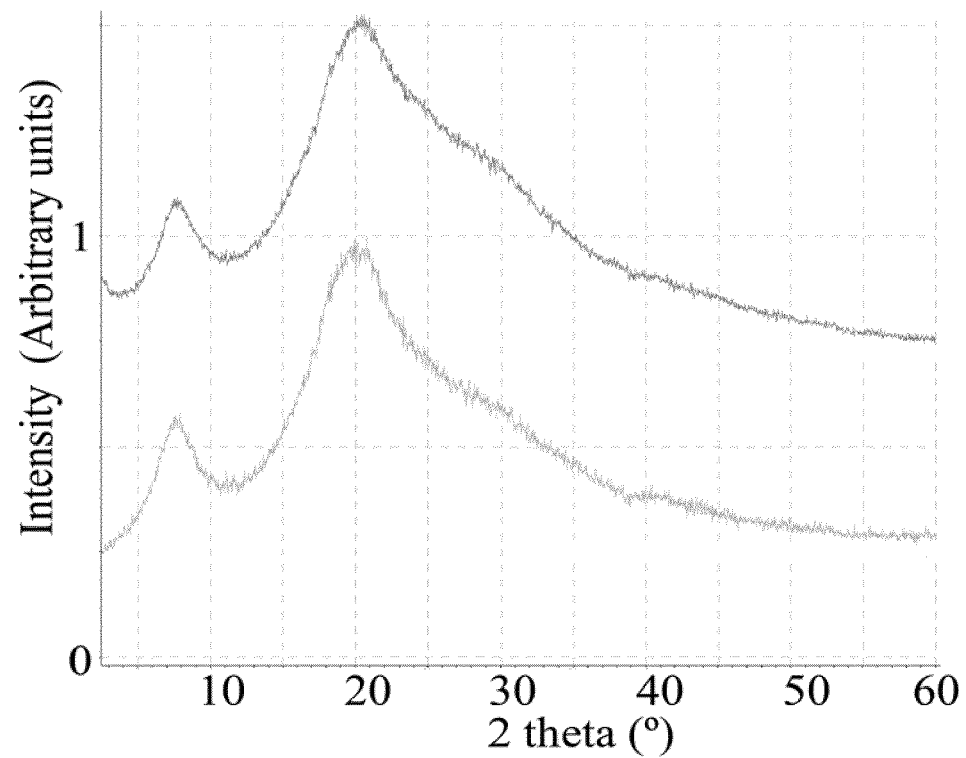
FIG. 9 illustrates a powder spectrum of an amorphous form of SEQ ID NO:1.

An amorphous form of SEQ ID NO:1 can have an XRPD pattern showing a lack of crystallinity. For example, an amorphous form has an XRPD pattern substantially the same as depicted in FIG. 9. In another embodiment, the amorphous form of the present invention has a broad diffuse peak with 2 theta values from about 10 to about 40°.

Further, an amorphous form of SEQ ID NO: 1 can comprise at least one endotherm and at least one exotherm, as can be observed by differential scanning calorimetry (DSC).

Such amorphous forms can have a glass transition temperature range of about 50° C. to about 60° C. In one embodiment, the glass transition temperature has a range of about 50° C. to about 58° C., or preferably, about 51° C. to about 57.5° C.

The amorphous forms described herein can also have a melting point range of about 125° C. to about 135° C. In one embodiment, the melting point range of the amorphous forms described herein are from about 129° C. to about 134° C.

Further amorphous forms described herein have chemical stability.

In one aspect, the present invention contemplates an amorphous form wherein the form has at least one property selected from:
(1) an XRPD pattern showing a lack of crystallinity;
(2) at least one endotherm and at least one exotherm observed by differential scanning calorimetry (DSC);
(3) a glass transition temperature range of about 51° C. to about 58° C.;
(4) a melting point range of about 129° C. to about 134° C.;
(5) a DSC or TGA substantially similar at least one of FIGS. 10-12; and
(6) chemical stability.

Processes for preparing amorphous forms described herein may in some aspects utilize removal of the used solvent by rapid solvent evaporation, spray drying, roller drying, solvent precipitation or freeze drying.

In one aspect, the present invention describes a process for preparing an amorphous form of a peptide comprising, consisting essentially of, or consisting of a SEQ ID NO: 1 comprising the steps of:
(a) heating a solution of the peptide comprising, consisting essentially of, or consisting of SEQ ID NO: 1 in a solvent, such as ethanol, 2-propanol, ethyl acetate and dichloromethane to obtain the amorphous form; and
(b) recovering the amorphous form.

Also described herein is a process for preparing an amorphous form of a peptide comprising, consisting essentially of, or consisting of a SEQ ID NO: 1 comprising the steps of:
(a) cooling a solution of the peptide comprising, consisting essentially of, or consisting of SEQ ID NO: 1 in a solvent such as water, toluene, hexane, chloroform, ethyl acetate, and ethanol to obtain the amorphous form; and
(b) recovering the amorphous form.

A further process for preparing an amorphous form of a peptide comprising, consisting essentially of, or consisting of SEQ ID NO: 1 comprising the steps of:
(a) acidifying a solution of the peptide comprising, consisting essentially of, or consisting of SEQ ID NO: 1 with an acid in a solvent such as acetonitrile and acetonitrile:water;
(b) cooling the solution to obtain the amorphous form; and
(c) recovering the amorphous form.

Suitable acids can include, by way of example, HCl and $H_2SO_4$.

A further process for preparing an amorphous form of a peptide comprising, consisting essentially of, or consisting of SEQ ID NO: 1 comprising the steps of:
(a) acidifying a solution of the peptide comprising, consisting essentially of, or consisting of SEQ ID NO: 1 with an acid in methanol;
(b) cooling the solution to obtain the amorphous form; and
(c) recovering the amorphous form.

Acids contemplated for use in preparing an amorphous form as described directly above can be HCl and $H_2SO_4$ or preferably HCl.

Acidifying solutions can include methanol and HCl at a molar ratio of about 1:4 to about 4:1 methanol:HCl. Such ratios can include 1:3, 1:2:1:1, 2:1, 3:1, or 4:1 methanol:HCl.

The present invention also contemplates a closed cycle spray drying system which can recycle the drying medium and may be used in terms of safety and economical efficiency of the process. In spray drying, an inert gas such as argon, nitrogen and carbon dioxide or air may be used as a drying gas. Inflow and outflow temperatures thereof may be dependent on the boiling point of the solvent used. For example, the inflow temperature may range from about 50° C. to about 140° C. and the outflow temperature may range from about 45° C. to about 100° C.

In one aspect of the present invention, freeze drying may be carried out at a suitable temperature depending on the freezing point of the solvent used.

In one embodiment of the present invention, recovery of the amorphous form can be achieved by removal of the solvent. In another embodiment of the present invention, recovery of the amorphous form may be achieved by drying of the amorphous form under atmospheric pressure or in vacuo. The recovery of the amorphous form may also be achieved under a stream of an inert gas, such as nitrogen.

The compositions (e.g., amorphous forms of SEQ ID NO:1) herein can be used to treat a condition in a patient. Such a condition can be pain, neuropathic or neurological disorder (e.g., Alzheimer's), addiction, neoplasm (e.g., cancer), and temperature regulation (e.g., fever, menopause syndromes, Reynaud's syndrome etc.). In the treatment of pain, the compositions herein can also be used as an analgesic or anesthetic.

Pharmaceutical Compositions

The active agents (i.e., the crystalline forms or amorphous forms, or mixtures thereof, of the peptide having a SEQ ID NO:1) of the invention may be formulated into pharmaceutical compositions suitable for pharmaceutical, veterinary, cosmetic, agricultural and human medical use. Pharmaceutical compositions of the invention can comprise a therapeutically effective amount of the active agent and one or more inert, pharmaceutically acceptable carriers, and optionally any other therapeutic ingredients, stabilizers, or the like.

In one aspect, the present invention contemplates a pharmaceutical composition comprising a peptide comprising, consisting essentially of, or consisting of SEQ ID NO:1 and a pharmaceutically acceptable carrier or excipient. In one embodiment, the invention provides a pharmaceutical composition comprising a peptide comprising, consisting essentially of, or consisting of SEQ ID NO:1 and at least one cation. Such cations can be any 2+ cation. Examples include $Ba^{2+}$, $Ca^{2+}$, $Cr^{2+}$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, and $Zn^{2+}$ and a pharmaceutically acceptable excipient or carrier. Preferable cations include $Mg^{2+}$ or $Zn^{2+}$.

Typically such formulations include one or more acceptable carriers, excipients, or diluents. Pharmaceutically acceptable carriers for therapeutic use are well known in the pharmaceutical art, and are described, e.g., in *Remington's Pharmaceutical Sciences*, Gennaro, A R, ed., 20th edition, 2000: Williams and Wilkins Pa., USA. which is incorporate herein by reference for all purposes. Agriculturally acceptable carriers for therapeutic or prophylactic treatment of plants are also known in the art. Cosmetic and veterinary excipients are also known in the art.

A pharmaceutical or agricultural formulation can also contain any kind of other compatible ingredients such as, for example, protective colloids, adhesives, thickening agents, thixotropic agents, penetrating agents, stabilizing agents, sequestering agents, fertilizers, anti-freeze agents, repellents, color additives, corrosion inhibitors, water-repelling agents, UV-stabilizers, pigments, dyes or polymers.

While any suitable carrier known may be employed in a pharmaceutical formulation of this invention, the type of carrier will vary depending on the mode of administration and whether a sustained release is desired. Routes of delivery may include oral, inhaled, buccal, intranasal, and transdermal routes, as well as novel delivery systems such as the protective liposomes for oral delivery of peptides.

For agricultural uses, formulations are preferably in a liquid or spray or any other dry formulations.

For parenteral administration, such as subcutaneous injection, the carrier preferably comprises water, saline, alcohol, a fat, a wax or a buffer.

For oral administration, a carrier preferably comprises of carbohydrate or polypeptide fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and polypeptides such as gelatin and collagen. If desired, disintegrating or solubilizing agents may be added, such as the cross-linked polyvinyl pyrrolidone, agar, alginic acid, or a salt thereof, such as sodium alginate. If desirable, the drug can be delivered in nanocapsules that would protect against proteolysis by proteases. Such carriers enable the compositions herein to be formulated as tablets, pills, dragees, capsules, liquids, gels, syrups, slurries, suspensions, and the like, for ingestion by the patient. Pharmaceutical preparations for oral use can be obtained through a combination of active compounds with solid excipient, suiting mixture is optionally grinding, and processing the mixture of granules, after adding suitable auxiliaries, if desired, to obtain tablets or dragee cores. As the composition may be peptide, such peptides are preferably put into a liposomal formulation to avoid degradation.

Preferably the pharmaceutical formulations herein are administration by intravenous injection or by local applications (e.g., topical or subdermal).

Formulations for topical administration can use a carrier that is a solution, emulsion, and ointment or gel base. The base, for example, may comprise one or more of the following: petrolatum, lanolin, PEGs, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 μm.

Pharmaceutical compositions may also contain diluents such as buffers, antioxidants such as ascorbic acid, low molecular weight (less than about 10 residues) polypeptides, polypeptides, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

Pharmaceutically acceptable formulations include compositions wherein the active ingredients (e.g., a crystalline or amorphous form comprising of, consisting essentially of, or consisting of SEQ ID NO:1) are contained in an effective dose to achieve the intended purpose. The determination of an effective amount or dosage is well within the capability of those skilled in the art. Typically, an effective dose of a composition of the present invention (e.g., a crystalline or amorphous form comprising of, consisting essentially of, or consisting of a peptide having a SEQ ID NO:1) for systemic administration is between about 0.001 µg to about 100 g, or more preferably between about 0.01 µg to about 50 g, or more preferably between about 0.1 µg to about 1 g, or more preferably between about 1 mg to about 500 mg per dose. For topical administration, the compositions herein may be delivered at dosage up to about 99, about 95, about 90, about 80, about 70, about 60, about 50, about 40, or about 30% w/w of the composition.

In some embodiments, the therapeutic effective dosages of a crystalline or amorphous form or a mixture thereof of a peptide comprising, consisting essentially of, or consisting of SEQ ID NO: 1 are the serum concentrations that in the range of about 1 to about 1000 mg/L, about 5 to about 500 mg/L, or about 10 to about 100 mg/L, or about 10 to about 20 mg/L of the active ingredient.

Any of the compositions herein may be co-formulated or co-administered with a second therapeutic agent. Examples of therapeutic agents include, but are not limited to, analgesic, antipyretic medicaments (fever reducers), anesthetics, anti-rheumatic agents, anti-inflammatory agents, antidepressants, anti-neoplastic agents, antimicrobial agents (e.g., antibiotics, antiviral agents, and antifungal agents), pesticides, herbicides, angiogenic agents, anti-angiogenic agents, inhibitors of neurotransmitters or neurotransmitters, any agent known to treat neurodegenerative conditions and wound healing, and combinations thereof.

For any of the compositions herein, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans. Those of ordinary skill in the art are well able to extrapolate from one model (be it an in vitro or an in vivo model). A therapeutically effective dose refers to that amount of active ingredient, for example a crystalline or amorphous form or a mixture thereof comprising of, consisting essentially of, or consisting of SEQ ID NO:1, which ameliorates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Pharmaceutically and physiologically acceptable compositions, which exhibit large therapeutic indices, are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The practitioner, in light of factors related to the subject that requires treatment, will determine the exact dosage. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. Long-acting pharmaceutically and physiologically acceptable compositions maybe administered every 3 to 4 days, every week, or once every two weeks depending on half-life and clearance rate of the particular formulation.

Normal dosage amounts may vary from about 0.001 µg to about 100 g, up to a total dose of about 1 g, depending upon the route of administration. Guidance as to particular dosages and methods of delivery is provided in the literature and generally available to practitioners in the art.

For example, for the prevention or treatment of pain, the appropriate dosage of the pharmaceutical compositions described herein will depend on the type of condition to be treated, as defined above, the severity and course of the disease, whether the agent is administered for preventive or therapeutic purposes or, as a combination with other drugs, previous therapy, the patient's clinical history and response to the agent, and the discretion of the attending physician. The agent is suitably administered to the patient at one time or over a series of treatments.

Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" in *Toxicokinetics and New Drug Development*, Yacobi et al., eds., Pergamon Press, New York 1989, pp. 42-96. For example, depending on the type and severity of the disease, about 0.001 µg/kg to about 1000 mg/kg of a therapeutic agent is an initial candidate dosage for administration to the patient, whether, for example, by one or more separate administrations, or by continuous infusion. A typical daily dosage might range from about 1 g/kg to about 100 g/kg or more, depending on the factors mentioned above. For local administration or topical administration lower dosage may be required. For repeated administrations over several days or longer, depending on the condition, the treatment is sustained until a desired suppression of disease symptoms occurs. However, other dosage regimens may be useful. The progress of this therapy is easily monitored by conventional techniques and assays. Guidance as to particular dosages and methods of delivery is provided in the literature; see, for example, U.S. Pat. Nos. 4,657,760; 5,206,344; or U.S. Pat. No. 5,225,212. It is anticipated that different formulations will be effective for different treatment compounds and different disorders, that administration targeting one organ or tissue, for example, may necessitate delivery in a manner different from that to another organ or tissue.

The compositions may be administered in the form of a solid, liquid, gel or gas (aerosol). The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to the compositions herein one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Injectable formulations of the compositions herein are preferably sterile. Means for achieving sterility are well known in the art.

For delivery to the dermis and/or epithelium, dermal patches and delivery systems, utilizing active or passive transdermal delivery carriers may be prepared suing well known methods and materials, including, for example, microporous membranes, silicon polymers and diffusion matrixes. Such materials and methods are described, for example, in: *Remington's Pharmaceutical Sciences*, supra.

A further aspect of the present invention relates to the use of a crystalline or amorphous form or a mixture thereof of a peptide comprising, consisting essentially of, or consisting of SEQ ID NO: 1 for preparing a pharmaceutical composition the treatment of disorders such as neurological disorders associated with pain and/or inflammation include, but are not limited to, Alzheimer's disease, amnesia, Aicardi syndrome, amyotrophic lateral sclerosis (Lou Gehrig's disease), anencephaly, anxiety, aphasia, arachnoiditis, Arnold Chiari malformation, attention deficit syndrome, autism, Batten disease, Bell's Palsy, bipolar syndrome, brachial plexus injury, brain injury, brain tumors, Charcol-Marie tooth disease, depression, dystonia, dyslexia, encephalitis, epilepsy, essential tremor, Guillain-Barre syndrome, hydrocephalus, hyperhidrosis, Krabbes disease, learning disabilities, leukodystrophy, meningitis, Moebius syndrome, multiple sclerosis, muscular dystrophy, Parkinson's disease, peripheral neuropathy, obsessive compulsive disorder, postural orthostatic tachycardia syndrome, progressive supranuclear palsy, prosopagnosia, schizophrenia, shingles, Shy-Drager syndrome, spasmodic torticollis, spina bifida, spinal muscular atrophy, stiff man syndrome, synesthesia, syringomyelia, thoracic outlet syndrome, tourette syndrome, toxoplasmosis, and trigeminal neurolagia.

A further aspect of the present invention relates to the use of crystalline or amorphous form or a mixture thereof of a peptide comprising, consisting essentially of, or consisting of SEQ ID NO:1 for the preparation of a medicament for the treatment of to modulate or treat cardiovascular conditions. Examples of cardiovascular conditions associated with pain and/or inflammation include, but are not limited to, angina, arrhythmia, high blood pressure, stroke, congestive heart failure, atherosclerosis, peripheral artery diseases, high cholesterol levels, and heart attacks.

The present invention also contemplates the use of a crystalline or amorphous form or a mixture thereof of a peptide comprising, consisting essentially of, or consisting of SEQ ID NO:1 for the preparation of a medicament for the treatment of narcotic addiction, narcotic tolerance that is developed when an opiate is given repeatedly over a period of time, and narcotic dependence that is physically changing life habits.

Crystalline and amorphous forms of a peptide comprising, consisting essentially of, or consisting of SEQ ID NO:1 can be used for the preparation of a medicament for the treatment and modulation of pain, such as nociceptive (non-chronic) pain, neuropathic (chronic) pain, idiopathic pain, headaches, low back pain, cancer pain, arthritis pain, sprains, bone fractures, pain resulting from burns, pain associated with bumps, pain associated with bruises, inflammatory pain (e.g., from an infection or arthritic disorder), pain from obstructions, myofascial pain, pain from nerve trauma (e.g., dystrophy/causalgia), phantom limb pain, entrapment neuropathy (e.g., carpal tunnel syndrome), and peripheral neuropathy.

In the light of the pharmaceutical efficacy of SEQ ID NO:1, the present invention furthermore relates to the use of a crystalline or amorphous form or a mixture thereof of a peptide comprising, consisting essentially of, or consisting of SEQ ID NO:1 as a medicament.

Administration

The compositions (including formulations) herein can be administered systemically or locally to an animal by any means known in the art. For example, to an animal such as a human, the compositions herein can be administered parenterally (which includes subcutaneously, intravenously, intramuscularly, intrasternally, intracavernously, intrathecally, and intraurethrally), intracranially, intraorbitally, intracapsularly, intraspinally, intracisternally, intrapulmonaryly (via inhalation), orally, intravenously, intra-arterially, intramedullary, intrathecally, intraventricularly, intrameatally, transdermally, subcutaneously, intraperitoneally, intranasally, enterally, vaginally, sublingually, or rectally. Preferably, the compositions herein are administered to an animal topically, subdermally or intravenously. In some embodiments, the composition/formulations herein are administered using insert(s), bead(s), timed-release formulation(s), patch(es) or fast-release formulation(s).

The compositions/formulations herein are preferably administered in an effective dose. It will be evident to those skilled in the art that the number, frequency, and duration of administration will be dependent upon the response of the host.

For therapeutic delivery, agents at concentrations of about 0.01 µg/kg to about 1000 mg/kg body weight may be administered, typically by the intradermal, subcutaneous, intramuscular or intravenous route, or by other routes. A preferred dosage is about 1 µg/kg to about 1000 mg/kg, or about 5 µg/kg to about 500 mg/kg, or about 10 µg/kg to about 100 mg/kg.

Methods of Treatment

A further feature of the present invention is the structural detail of a crystalline or amorphous form or a mixture thereof of a peptide comprising, consisting essentially of, or consisting of SEQ ID NO:1 necessary to design a modulator with high potency and specificity. By exploiting the structural details obtained from the crystal structure, it would be possible to design a modulator that exploits its unique structural features. A modulator developed using the structural coordinates of a crystalline or amorphous form of a peptide comprising, consisting essentially of, or consisting of SEQ ID NO:1 may provide a starting point for the development of modulators of pain receptors. Such modulators can lead to therapeutic compounds to treat a wide range of conditions beside pain, including inflammation, malignancies. Other applications of a pain modulator developed in accordance with the present invention can be employed to treat pain and other neurological disorders, cognitive performance, memory and learning enhancement, addiction and dependence of narcotics.

In some aspects, the present invention relates to uses of compositions such as the crystalline or amorphous forms or a mixture thereof of a peptide comprising, consisting essentially of, or consisting of SEQ ID NO:1 for modulating, preventing, or treating condition(s) in an organism. Such organisms can be animals and/or plants. Animals are preferably domesticated animals or humans. Plants are preferably crops such as wheat, barley, rice, corn, sugar, or soy; vegetables or fruits, such as apples, pears, citrus fruits, berries and nuts; and/or flowering plants such as roses, gardenias, orchids, carnations, bird of paradise, etc. But other plants or parts of plants are also contemplated herein (e.g., trees for lumber, such as fir, redwoods, pine, etc.)

The conditions that are modulated, prevented, or treated by the compositions herein can be broadly classified as metabolic or mitochondrial conditions. More specifically, such conditions are e.g., thermogenic or pyrogenic conditions. Such conditions can be associated with, for example, pain, temperature regulation, inflammation, neoplastic growth (e.g., cancer), innate immune response activation and ability to fight parasites and pathogens, skin and dermatological conditions, diabetes related disorders, wound healing, undesirable drug side effects, and neurological and neurodegenerative conditions.

Such conditions can occur in a cell, group of cells, or an entire organism to be treated herein.

In some embodiments, the compositions herein (e.g., a crystalline or amorphous form or a mixture thereof of a peptide comprising of, consisting essentially of, or consisting of SEQ ID NO:1) are used to module or treat inflammatory conditions that may or may not cause pain. Such conditions may show one or more of the following symptoms: redness, heat, tenderness and swelling. Examples of such conditions include, but are not limited to, chronic inflammatory diseases, such as rheumatoid arthritis, inflammatory bowel disease, systemic lupus erythematosus, multiple sclerosis, and type I and II diabetes, asthma, and inflammatory diseases of the central nervous system such as multiple sclerosis, abscess, meningitis, encephalitis and vasculitis.

In some embodiments, the compositions herein (e.g., a crystalline or amorphous form or a mixture thereof of a peptide comprising of, consisting essentially of, or consisting of SEQ ID NO:1) are used to modulate or treat cardiovascular conditions. Examples of cardiovascular conditions associated with pain and/or inflammation include, but are not limited to, angina, arrhythmia, high blood pressure, stroke, congestive heart failure, atherosclerosis, peripheral artery diseases, high cholesterol levels, and heart attacks.

In some embodiments, the compositions herein (e.g., a crystalline or amorphous form or a mixture thereof of a peptide comprising of, consisting essentially of, or consisting of SEQ ID NO:1) are used to modulate or treat a neurological or neurodegenerative condition or a mental or behavioral disorder. Examples of neurological conditions associated with pain and/or inflammation include, but are not limited to, Alzheimer's disease, amnesia, Aicardi syndrome, amyotrophic lateral sclerosis (Lou Gehrig's disease), anencephaly, anxiety, aphasia, arachnoiditis, Arnold Chiari malformation, attention deficit syndrome, autism, Batten disease, Bell's Palsy, bipolar syndrome, brachial plexus injury, brain injury, brain tumors, childhood depresses ion, Charcol-Marie tooth disease, depression, dystonia, dyslexia, encephalitis, epilepsy, essential tremor, Guillain-Barre syndrome, hydrocephalus, hyperhidrosis, Krabbes disease, learning disabilities, leukodystrophy, meningitis, Moebius syndrome, multiple sclerosis, muscular dystrophy, Parkinson's disease, peripheral neuropathy, obsessive compulsive disorder, postural orthostatic tachycardia syndrome, progressive supranuclear palsy, prosopagnosia, schizophrenia, shingles, Shy-Drager syndrome, spasmodic torticollis, spina bifida, spinal muscular atrophy, stiff man syndrome, synesthesia, syringomyelia, thoracic outlet syndrome, tourette syndrome, toxoplasmosis, and trigeminal neurolagia.

Examples of mental and behavioral disorders include, but are not limited to, anxiety disorder, panic disorder, obsessive-compulsive disorder, post-traumatic stress disorder, social phobia (or social anxiety disorder), specific phobias, and generalized anxiety disorder. Any of the above conditions can also be accompanied by or manifested by other conditions such as depression, drug abuse, or alcoholism.

In some embodiments, the compositions herein are used to treat fever that occurs with many different conditions such as inflammation and infectious diseases.

In some embodiments, the compositions herein are used to modulate or treat neoplastic growth. Examples of neoplastic growth include, but are not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell leukemia, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforme, leukemias, lymphomas, malignant melanomas, epidermoid carcinomas, and other carcinomas and sarcomas.

While the invention has been described in connection with the embodiments found herein, it is not intended to limit the scope of the invention to the particular form set forth, but on the contrary, it is intended to cover such alternatives, modifications, and equivalents as may be included within the spirit and scope of the invention as defined by the appended claims.

EXAMPLES

The following examples are illustrative and non-limiting to the scope of the compositions and methods described herein:

Example 1

Structure of SEQ ID NO:1

SEQ ID NO:1 has the following structure and characteristics (FIG. 1):

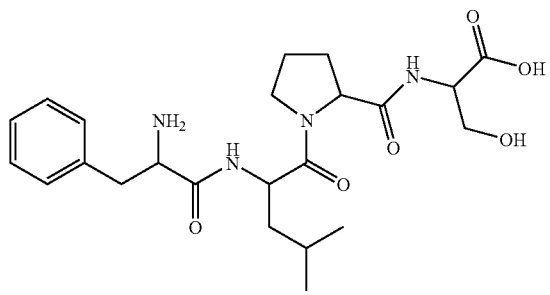

FIG. 1 illustrates the formula of SEQ ID NO:1. Formula, $C_{23}H_{34}N_4O_6$; composition, C, 59.72; H, 7.41; N, 12.11; O, 20.75; Molecular Weight 462.54; Exact Mass 462.25.

Example 2

Crystallization and Data Collection

Statistics of crystallographic data and structure of two types of crystals of SEQ ID NO:1 is as follows Crystal 1:

The SEQ ID NO:1 crystals were grown in room temperature in a 96 well plate containing 1 μL of 60 mg/ml of the peptide and 1 ml of the reservoir. Crystals appeared after several days and continuously grew to a size up to 0.50×0.24× 0.12 mm. Before data collection, crystals were mounted on a glass capillary with oil and frozen in liquid nitrogen. Data was collected at −143° C. with two sets of exposure. Crystal-to-detector distance was 35 mm and exposure time was 60 seconds per degree for all sets. The scan width was 1.5 per frame. Data collection was 98.9% complete to 25° in ∂. A total of 84019 partial and complete reflections were collected covering the indices, h=−12 to 12, k=−29 to 31, 1=−25 to 25. 17588 reflections were symmetry independent and the $R_{int}$=0.146 indicated that the data was sufficient. The resolution limit is 0.83 Å. The data was integrated and scaled using hkl-SCALEPACK. This program applies a multiplicative correction factor (S) to the observed intensities (I) and has the following form:

$$S = (e^{-2B(\sin^2\theta)/\lambda^2})/\text{scale}$$

S is calculated from the scale and the B factor determined for each frame and is then applied to I to give the corrected intensity ($I_{corr}$). Solution by direct methods (SHELXS97) produced a complete heavy atom phasing model with motives of the proposed structure. All hydrogen atoms were located using a riding model. All non-hydrogen atoms were refined anisotropically by full-matrix least-squares. Indexing and unit cell refinement indicated a monoclinic P lattice. The crystals formed in the $P2_1$ with a=10.0440 Å b=25.946 Å c=20.82 Å α=γ=90 degree β=91.9461 Å. In this type, each asymmetry unit contains 4 molecules of SEQ ID NO:1. FIG. 2 depicts the coordination complex of SEQ ID NO:1 with zinc in the crystalline form. As shown in FIG: 2, the peptides form a Zn complex. 4 peptides, 2 $Zn^{2+}$, an ethanol molecule, and 8 waters complete the asymmetric unit as shown in the graph. Two complexes fill the unit cell. The carboxyl groups loose the hydrogen and the complex extends infinitesimally through the crystal connected by $Zn^{2+}$. The hydrogen atoms on N1, N5, N9, N13 were identified partially by electron density peaks and stay whereas the bond distances of the carboxyl oxygen atoms are too short for presence of a hydroxyl group. The charge of the two lost hydrogen atoms from two peptides is balanced by that of the $Zn^{2+}$, however, lone-pair bonding to the $Zn^{2+}$ is found in addition to the nitrogens N1, N5, N9, N13 also in the ketones O1, O4, (O7), O10, O13, O16, (O19), O22. Disorder on the hydroxyl group O12/O34 is related to the half-site occupancy of the ethanol (O25). The structure was edited to satisfy requirements for publication in Acta Cryst. The 4 peptides are similar to each other, as shown in FIG. 3. The peptides are shown together with the Zn ions which are shared between the peptides. The S-amino acid shows strongest conformational differences between peptides.

Crystal 2:

The SEQ ID NO:1 crystals were grown in room temperature in a 96 well plate containing 1 μL of 60 mg/ml of the peptide and 1 ml of the reservoir. Crystals appeared after several days and continuously grew to a size up to 0.36×0.20× 0.15 mm. A clear prism was mounted on a glass capillary with oil. Data was collected at −143° C. Crystal-to-detector distance was 35 mm and exposure time was 20 seconds per degree for all sets. The scan width was 2°. Data collection was 96.6% complete to 25° in ∂. A total of 56983 partial and complete reflections were collected covering the indices, h=−11 to 11, k=−21 to 24, 1=−29 to 30. 8649 reflections were symmetry independent and the $R_{int}$=0.2162 indicated that the data was of less than average quality (0.07) due to the fact that it consisted mainly of carbon and hydrogen. The data was integrated and scaled using hkl-SCALEPACK. This program applies a multiplicative correction factor (S) to the observed intensities (I) and has the following form:

$$S = (e^{-2B(\sin^2\theta)/\lambda^2})/\text{scale}$$

S is calculated from the scale and the B factor determined for each frame and is then applied to I to give the corrected intensity ($I_{corr}$). Solution by direct methods (SHELXS97) produced an almost complete heavy atom phasing model consistent with the proposed structure. All hydrogen atoms were located using a riding model. All non-hydrogen atoms were refined anisotropically by full-matrix least-squares. Indexing and unit cell refinement indicated a monoclinic P lattice. The crystals formed in the $P2_12_12_1$ with a=9.9290 Å b=20.4060 Å c=25.827 Å; α=β=γ=90 degree. In this type each asymmetry unit contain 2 molecules of SEQ ID NO:1. FIG. 4 shows the asymmetric unit of a second type of hydrated crystalline SEQ ID NO:1. The peptide complex shows disorder accordingly affecting one hydroxy group (O6 is disordered with O18) at a ratio of almost 1:3 and a phenol group (C27-C32 is disordered with C127-C132) at a ratio of roughly 1:1. Not shown in FIG. 4 are 4 waters and one alcohol. The alcohol is disordered at a concentration of 43% with one water at 57%. (moiety formula: $2(C_{23}H_{33}N_4O_6)$ Zn, $0.43(C_2H_5OH)$, $3.57(H_2O)$. The peptide complex shows disorder accordingly affecting one hydroxy group (O6 is disordered with O18) at a ratio of almost 1:3 and a phenol group (C27-C32 is disordered with C127-C132) at a ratio of roughly 1:1. The structure was edited for publication to comply with IUCr requirements. FIG. 5 shows the peptides individually (without disorder).

FIG. 6 shows the arrangement of the second type of crystal including solvents and disorder (Zn is yellow here). It is visible that one Zn atom coordinates with four peptides, i.e. two peptides via the lone pairs of N1/O1/or N5/O7 and two via lone pairs of O5 and O10 giving Zn an octahedral coordination. The coordination sequence continues throughout the crystal leading to quasiinfinite linear strings of Zn-coordinated peptides.

Example 3

Calculated Powder Spectrum of Hydrated Crystal Form of SEQ ID NO:1

FIG. 7 depicts a calculated powder spectrum of hydrated crystal form of SEQ ID NO:1 which is calculated for Cu radiation.

Example 4

Data for Amorphous Form

The present invention relates to the solid state physical properties of SEQ ID NO:1. The SEM image of SEQ ID NO:1 in amorphous forms are shown in FIG. 8.

Example 5

Nuclear Magnetic Resonance (NMR)

Samples were prepared for $^1$H NMR spectroscopy as ~5-50 mg solutions in the appropriate deuterated solvent.

A typical $^1$H-NMR spectrum of SEQ ID NO: 1 is shown in Table 1., Chemical shifts and integrated intensity were found to be consistent with the structure of SEQ ID NO:1.

TABLE I

¹H NMR analysis in CD₃OD with TMS of SEQ ID NO: 1.

| Frequency | PPM | Height |
|---|---|---|
| 3280.371 | 8.205 | 4.1 |
| 3272.656 | 8.186 | 4.0 |
| 2959.473 | 7.403 | 5.7 |
| 2951.465 | 7.382 | 31.7 |
| 2949.512 | 7.378 | 36.8 |
| 2947.852 | 7.373 | 18.9 |
| 2945.020 | 7.366 | 41.6 |
| 2942.773 | 7.361 | 108.7 |
| 2941.016 | 7.356 | 64.0 |
| 2937.012 | 7.346 | 54.6 |
| 2935.645 | 7.343 | 132.0 |
| 2933.203 | 7.337 | 35.9 |
| 2932.227 | 7.334 | 40.3 |
| 2930.371 | 7.330 | 81.1 |
| 2928.809 | 7.326 | 70.5 |
| 2926.270 | 7.319 | 24.7 |
| 2923.535 | 7.313 | 69.3 |
| 2919.824 | 7.303 | 19.5 |
| 2917.578 | 7.298 | 18.0 |
| 2916.016 | 7.294 | 30.1 |
| 2913.965 | 7.289 | 115.5 |
| 2912.207 | 7.284 | 121.0 |
| 2909.961 | 7.279 | 29.6 |
| 2905.859 | 7.268 | 83.5 |
| 1951.660 | 4.882 | 3542.9 |
| 1897.852 | 4.747 | 50.3 |
| 1892.871 | 4.735 | 51.6 |
| 1883.477 | 4.724 | 54.5 |
| 1883.398 | 4.711 | 51.8 |
| 1855.273 | 4.641 | 7.2 |
| 1851.660 | 4.632 | 7.1 |
| 1844.727 | 4.614 | 7.8 |
| 1841.309 | 4.606 | 6.8 |
| 1829.199 | 4.575 | 5.6 |
| 1824.121 | 4.563 | 12.8 |
| 1821.582 | 4.556 | 10.0 |
| 1815.527 | 4.541 | 70.4 |
| 1810.937 | 4.530 | 59.1 |
| 1806.934 | 4.520 | 70.4 |
| 1804.785 | 4.514 | 39.5 |
| 1802.930 | 4.510 | 58.3 |
| 1793.652 | 4.486 | 7.2 |
| 1788.574 | 4.474 | 73.1 |
| 1784.766 | 4.464 | 127.1 |
| 1780.371 | 4.453 | 73.8 |
| 1712.598 | 4.284 | 4.3 |
| 1655.762 | 4.142 | 60.8 |
| 1650.684 | 4.129 | 75.2 |
| 1646.973 | 4.120 | 80.4 |
| 1641.895 | 4.107 | 67.5 |
| 1636.230 | 4.093 | 12.2 |
| 1631.445 | 4.081 | 9.4 |
| 1607.520 | 4.021 | 4.5 |
| 1596.289 | 3.993 | 16.2 |
| 1591.602 | 3.981 | 17.6 |
| 1590.430 | 3.978 | 17.5 |
| 1586.230 | 3.968 | 15.9 |
| 1579.102 | 3.950 | 6.0 |
| 1574.902 | 3.939 | 65.7 |
| 1570.410 | 3.928 | 62.5 |
| 1563.574 | 3.911 | 110.2 |
| 1559.082 | 3.900 | 100.0 |
| 1544.531 | 3.863 | 20.4 |
| 1539.258 | 3.850 | 121.4 |
| 1535.352 | 3.840 | 132.0 |
| 1531.348 | 3.830 | 35.1 |
| 1527.930 | 3.822 | 109.8 |
| 1524.121 | 3.812 | 68.6 |
| 1521.680 | 3.806 | 25.8 |
| 1484.180 | 3.712 | 4.2 |
| 1482.520 | 3.708 | 4.5 |
| 1474.902 | 3.689 | 21.9 |
| 1469.336 | 3.675 | 39.7 |
| 1465.723 | 3.666 | 27.3 |
| 1462.109 | 3.657 | 33.8 |
| 1459.766 | 3.651 | 34.2 |
| 1452.539 | 3.633 | 18.2 |
| 1329.004 | 3.324 | 65.1 |
| 1327.734 | 3.321 | 66.9 |
| 1327.344 | 3.320 | 105.8 |
| 1326.953 | 3.319 | 112.1 |
| 1326.562 | 3.318 | 137.8 |
| 1326.172 | 3.317 | 182.3 |
| 1324.609 | 3.313 | 2469.0 |
| 1322.949 | 3.309 | 4969.0 |
| 1321.289 | 3.305 | 7195.8 |
| 1320.410 | 3.303 | 1145.5 |
| 1319.629 | 3.301 | 4962.4 |
| 1317.969 | 3.297 | 2481.2 |
| 1316.797 | 3.294 | 186.7 |
| 1316.309 | 3.292 | 136.5 |
| 1315.918 | 3.292 | 108.9 |
| 1315.527 | 3.291 | 94.6 |
| 1315.137 | 3.290 | 90.1 |
| 1314.746 | 3.289 | 95.0 |
| 1314.355 | 3.288 | 109.9 |
| 1313.965 | 3.287 | 123.3 |
| 1313.574 | 3.286 | 122.4 |
| 1313.184 | 3.285 | 103.2 |
| 1312.402 | 3.283 | 59.9 |
| 1304.395 | 3.263 | 118.0 |
| 1299.219 | 3.250 | 105.7 |
| 1202.051 | 3.007 | 117.1 |
| 1193.262 | 2.985 | 114.8 |
| 1187.598 | 2.971 | 97.7 |
| 1173.906 | 2.949 | 90.9 |
| 908.398 | 2.272 | 6.8 |
| 903.906 | 2.261 | 6.9 |
| 900.879 | 2.253 | 8.3 |
| 896.777 | 2.243 | 8.1 |
| 893.066 | 2.234 | 9.1 |
| 882.031 | 2.206 | 4.4 |
| 853.613 | 2.135 | 3.6 |
| 846.777 | 2.118 | 6.9 |
| 834.082 | 2.086 | 15.1 |
| 830.469 | 2.077 | 16.2 |
| 824.023 | 2.061 | 13.7 |
| 818.359 | 2.047 | 9.3 |
| 804.883 | 2.013 | 6.7 |
| 797.754 | 1.995 | 9.2 |
| 791.992 | 1.981 | 6.9 |
| 712.109 | 1.781 | 6.7 |
| 704.395 | 1.762 | 8.6 |
| 698.047 | 1.746 | 8.6 |
| 691.602 | 1.730 | 5.8 |
| 680.469 | 1.702 | 5.0 |
| 675.586 | 1.690 | 6.5 |
| 666.504 | 1.667 | 18.4 |
| 661.816 | 1.655 | 26.5 |
| 658.495 | 1.647 | 15.8 |
| 656.152 | 1.641 | 15.1 |
| 652.832 | 1.633 | 21.8 |
| 647.168 | 1.619 | 13.3 |
| 638.477 | 1.597 | 4.9 |
| 402.539 | 1.007 | 110.1 |
| 397.559 | 0.994 | 132.0 |
| 395.995 | 0.991 | 126.7 |
| 391.113 | 0.978 | 112.1 |
| 386.035 | 0.966 | 14.2 |

The peaks at 4.882 ppm and 3.309, 3.305, and 3.301 ppm are attributed to deuterated methanol.. The peak marked 0.000 ppm is attributed to TMS as a reference. Deviations were observed in ±1 ppm range.

Example 6

Approximate Solubility—Solvent Addition Method

A weighed sample of SEQ ID NO:1 (a polypeptide of amino acids F-L-P—S) was treated with aliquots of the test solvent at ambient temperature. Complete dissolution of the test material was determined by visual inspection. Solubility was estimated based on the total solvent used to provide complete dissolution. The actual solubility may be greater than the value calculated because of the use of solvent aliquots that were too large or due to a slow rate of dissolution. The solubility is expressed as "less than" if dissolution did not occur during the experiment. If complete dissolution was achieved as a result of only one aliquot addition, the solubility is expressed as "greater than".

It is soluble in many solvents such as those with different polarity (Table II).

TABLE II

Solubility of SEQ ID NO: 1 in different solvents.

| Solvent | Solubility (mg/ml) |
|---|---|
| Water | $\geq 60$ |
| Methanol (MeOH) | $\geq 50$ |
| Ethanol (EtOH) | $\geq 52$ |
| 2-Propanol | $\geq 20$ |
| 2-Butanone | $\geq 20$ |
| Ethyl acetate (EtOAc) | $\geq 20$ |
| Dichloromethane (DCM) | $\geq 20$ |
| Chloroform | $\leq 1.9$ |
| Tetrahydrofuran (THF) | $\geq 44$ |
| 1-Butanol | $\geq 43$ |
| Isopropyl ether | $\leq 2.7$ |
| Acetone | $\geq 40$ |
| Acetonitrile (ACN) | $\geq 19$ |
| Pentane | $\leq 2.0$ |
| Heptane | $\leq 2.0$ |
| Toluene | $\leq 3.6$ |

Example 7

X-Ray Powder Diffraction (XRPD)

X-ray powder diffraction analyses were performed on an Inel XRG-3000 diffractometer, equipped with a curved position-sensitive detector with a 2θ range of 120°. Real time data was collected using Cu Kα radiation at a resolution of 0.03°2θ. The tube voltage and amperage were set to 40 kV and 30 mA, respectively. Patterns are displayed from 2.5 to 60° 2θ to facilitate direct pattern comparisons. Samples were prepared for analysis by packing them into thin-walled glass capillaries. Each capillary was mounted onto a goniometer head that is motorized to permit spinning of the capillary during data acquisition. The samples were analyzed for 30 minutes. Instrument calibration was performed daily using a silicon reference standard.

X-ray powder diffraction (XRPD) analyses were also performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 1°/min (0.02° step) from 2.5 to 60° 2θ was used. A silicon standard was analyzed to check the instrument alignment. Data were collected and analyzed using XRD-6100/7000 v. 5.0. Samples were prepared for analysis by placing them in an aluminum holder with silicon insert.

The present invention provides a description of the x-ray amorphous form of SEQ ID NO:1 (FIG. 9).

Example 8

Thermal Analysis (a) Differential Scanning Calorimetry (DSC)

Analyses were carried out on a TA Instruments differential scanning calorimeter 2920 or Q1000. The instrument was calibrated using indium as the reference material. The sample was placed into a standard aluminum DSC pan with a non-crimped lid configuration, and the weight accurately recorded. The sample cell was equilibrated at 25° C. and heated under a nitrogen purge at a rate of 10° C./min, up to a final temperature of 350° C. To determine the glass transition temperature (Tg) of amorphous material, the sample cell was cycled between −50 and 110° C.

(b) Thermogravimetry (TG)

Analyses were carried out on a TA Instruments 2950 thermogravimetric analyzer. The calibration standards were nickel and Alumel™. Each sample was placed on an aluminum sample pan and inserted into the TG furnace. Samples were started at ambient, then heated under a dry nitrogen purge at a heating rate of 10 C./min, up to a final temperature of 350° C. unless specified otherwise.

Figure 10:
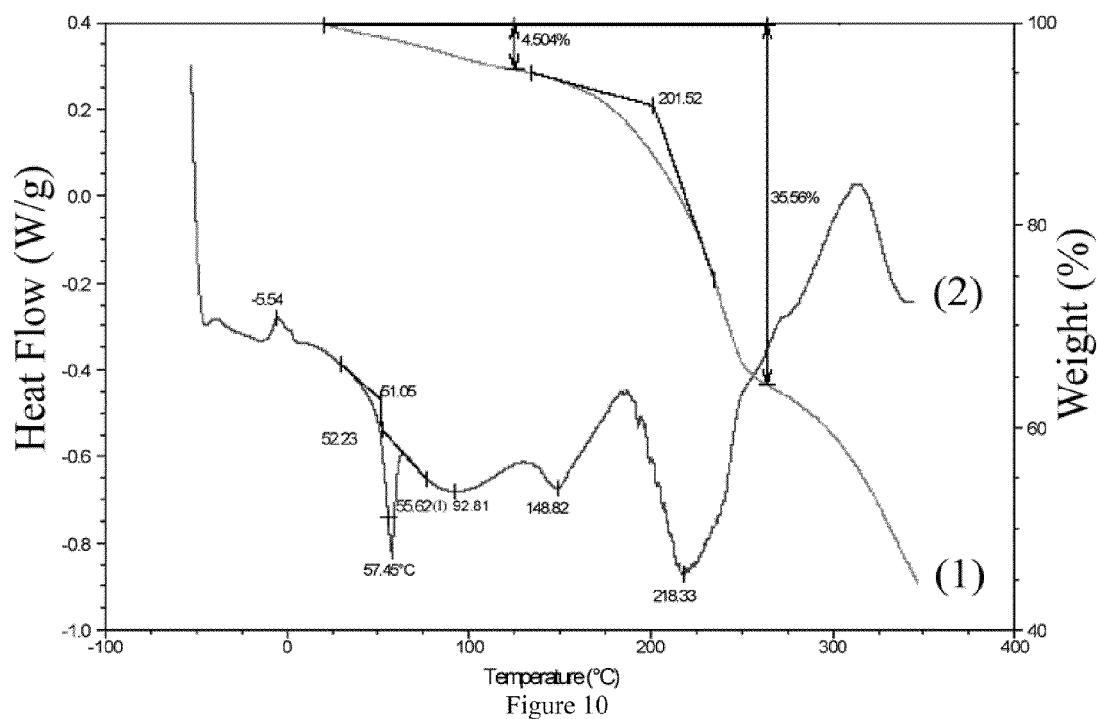
FIG. 10 Illustrates differential scanning calorimetry (DSC, line 1) and thermal gravimetric analysis (TGA, line 2) profiles of an amorphous SEQ ID NO:1.

In another aspect, the differential scanning calorimetry (DSC) using a single heating step and the thermal gravimetric analysis (TGA) profiles of the amorphous form of SEQ ID NO:1 are shown in FIG. 10. The DSC data shows four significant endotherms with the signal minima (e.g., peaks) of the thermogram occurring at approximately 57.5, 92.8, 148.8, and 218.3° C. The thermal event corresponding to the peak at 57.5° C. (onset: 51.1° C.) is consistent with the signature of a 'glass transition temperature', observed in highly disordered or amorphous materials, and denotes a significant change in the molecular mobility of the material as temperature is increased above 51.1° C. The thermal events corresponding to the signal peak at 218.3 C. are indicative of decomposition.

The DSC endotherm at 92.4° C. (peak) corresponds with the weight loss of approximately 4.5 w % from ambient temperature up to ~125° C. measured by TGA indicating the loss of one or more residual volatile component in the material on heating. The TGA shows that at 201.5° C. the decomposition of SEQ ID NO:1 takes place at higher temperature a 35.6 w % is observed.

Figure 11:
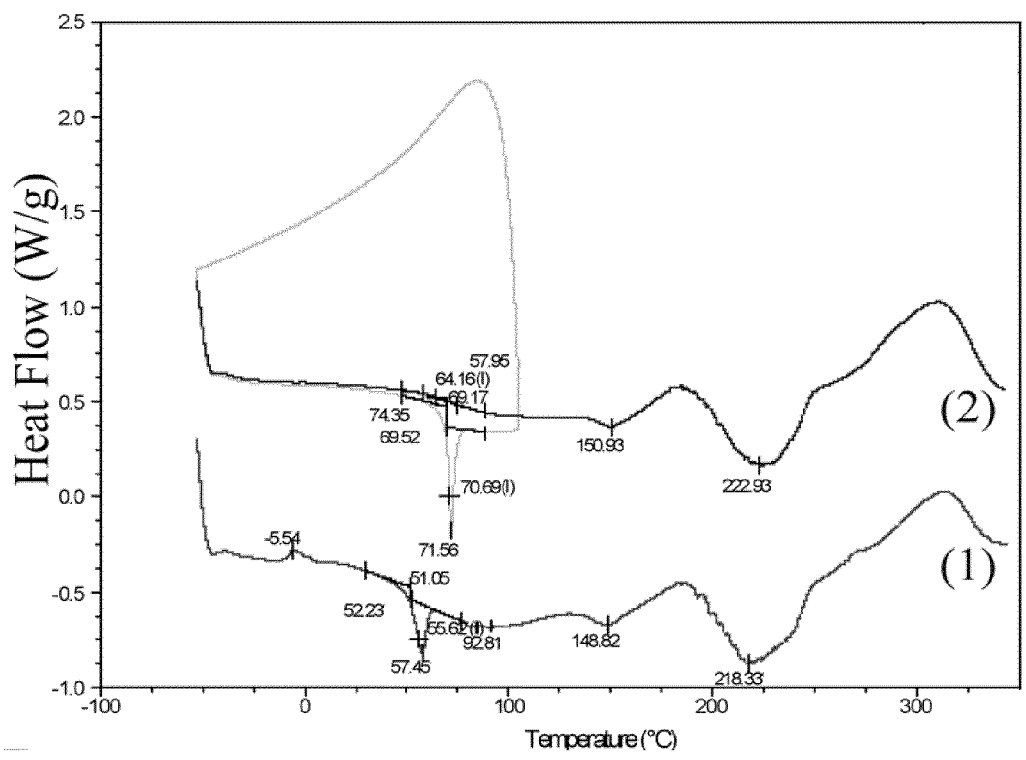
FIG. 11 illustrates differential scanning calorimetry (DSC) profiles of amorphous SEQ ID NO:1 with temperature cycling on the first day of receiving (line 1) and after 63 days stored at ambient temperature (line 2).

The DSC profiles of SEQ ID NO:1 using temperature cycling is shown in FIG. 11 under two conditions: immediately upon receiving (line 1) and after storage at ambient temperature for 63 days (line 2). The DSC data shows four significant endotherms with the signal minima (e.g., peaks) of the thermogram occurring at approximately 69.2, 71.6, 58, 150.9, and 222.9° C. On heating the material to 110° C., the thermal event associated with the apparent glass transition at 57.5° C. (peak in line 1) is observed to increase to 71.6° C. (peak in line 2) with an apparent increase in the relative magnitude (e.g., area under the curve) of the endotherm. This change is consistent with structural changes, termed 'relaxation', of disordered solids during storage. On cooling and subsequent re-heating of the material, no evidence of an endotherm associated with the peak at 71.6° C. was observed, which is consistent with removing the thermal history of a disordered solid when the temperature of the material is raised above and subsequently cooled below the glass transition temperature. Further, no evidence of the endotherm at ~92.8° C. (peak in line 1) was observed during the reheating step, which provides supporting evidence for this endotherm being attributed to the removal of a volatile component, such as water, during the first heating step.

Figure 12:
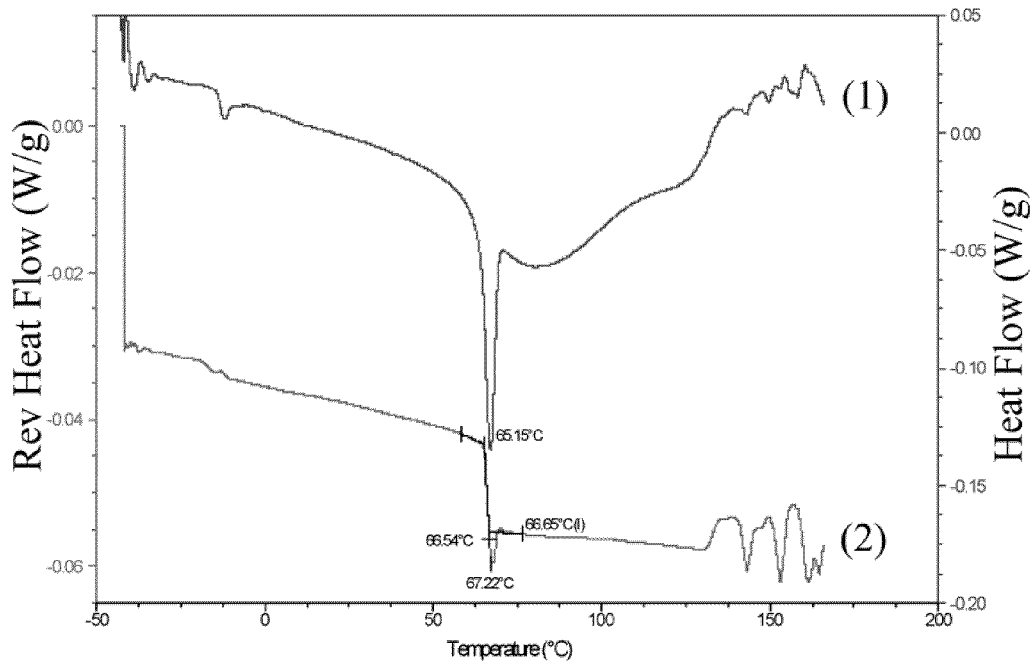
FIG. 12 illustrates the modulated DSC profiles of non-reversing and reversing heat flow of amorphous SEQ ID NO:1.

The modulated DSC data shows one significant endotherm with the signal minima (e.g., peaks) of the thermogram occurring at approximately 67.2 (FIG. 12).

Example 9

Dynamic Vapor Sorption/Desorption (DVS)

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. Sodium chloride and polyvinypyrrolidine were used as calibration standards.

Figure 13:
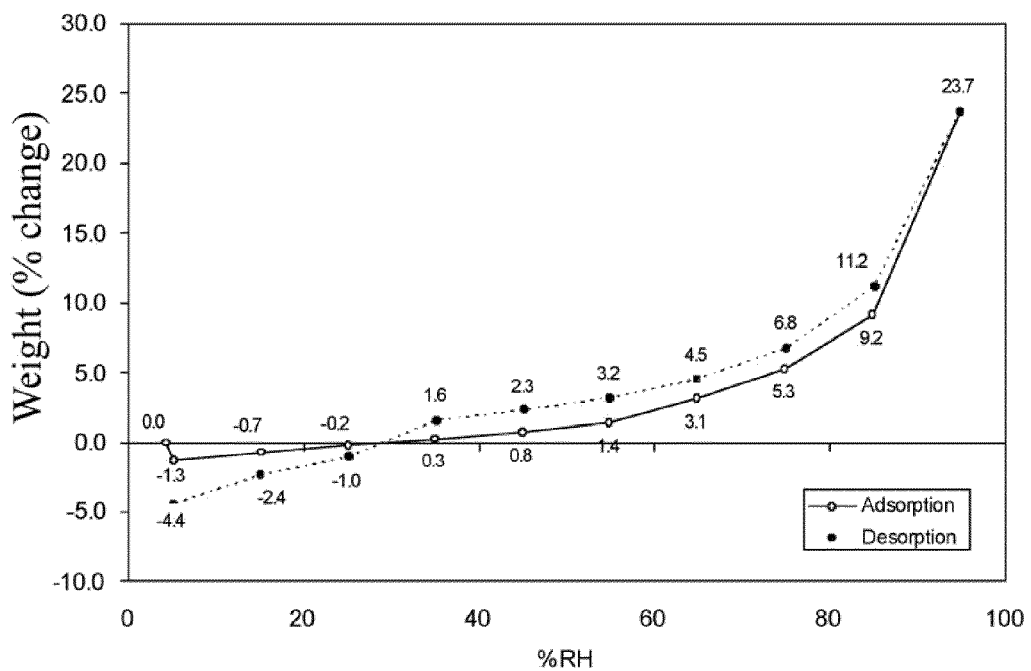
FIG. 13 illustrates the dynamic vapor sorption (DVS) of amorphous SEQ ID NO:1. Percent weight change during adsorption/desorption. Adsorption: 5→95% RH with 25.0 w% gain; Desorption: 95→5% RH with 28.2 w% loss.

The dynamic vapor sorption/desorption (DVS) data are shown in FIG. 13. The material exhibits an initial weight loss of 1.3%, suggesting that the as received material contained a residual amount of a volatile component that was not removed on equilibration at ~5% RH. This was followed by a steady weight gain of approximately 23.7% up to ~95% RH on the sorption step. During the desorption step, the material exhibits minor hysteresis with a final weight loss of 4.4%, which is less than the original weight at ~5% RH. Table III provides additional data on the weight gain and lost of SEQ ID NO:1 and is in support of the stability of SEQ ID NO:1.

Example 10

Energy Dispersive X-Ray Analysis (EDX)

Energy dispersive X-ray analysis (EDX) was performed using an EDAX™ X-ray detector mounted on an FEI Quanta 200 scanning electron microscope (SEM), and EDAX Genesis v. 3.5 software. Samples were prepared for analysis by placing a small amount on carbon double-stick tape fixed to an aluminum sample mount. The EDX analyses used a beam voltage of 20 kV, a spot size of 5.5 µm. Analysis time, recorded in detector live time, was 175 s. Under high vacuum mode, an Everhart Thomley (ET) detector was used for SEM. The resolution of the image was 1024×884. Both instruments were calibrated using NIST standards. SEM data was collected using x™ (v. 2.01), and analyzed using XT Docu (v. 3.2). Magnification reported on the SEM images were calculated upon the initial data acquisition. The scale bar reported in the lower portion of each image.

Example 11

Hot Stage Microscopy

Hot stage microscopy was performed using a Linkam hot stage (model FTIR 600) mounted on a Leica DM LP microscope. Samples were observed using a 20× objective (obj.) with cross polarizers (CP) and lambda (λ) compensator. Samples were placed on a coverslip. A second coverslip was then placed over the sample. Each sample was visually observed as the stage was heated. Images were captured using a SPOT Insight™ color digital camera with SPOT Software v. 4.5.9. The hot stage was calibrated using USP melting point standards.

Figure 14:
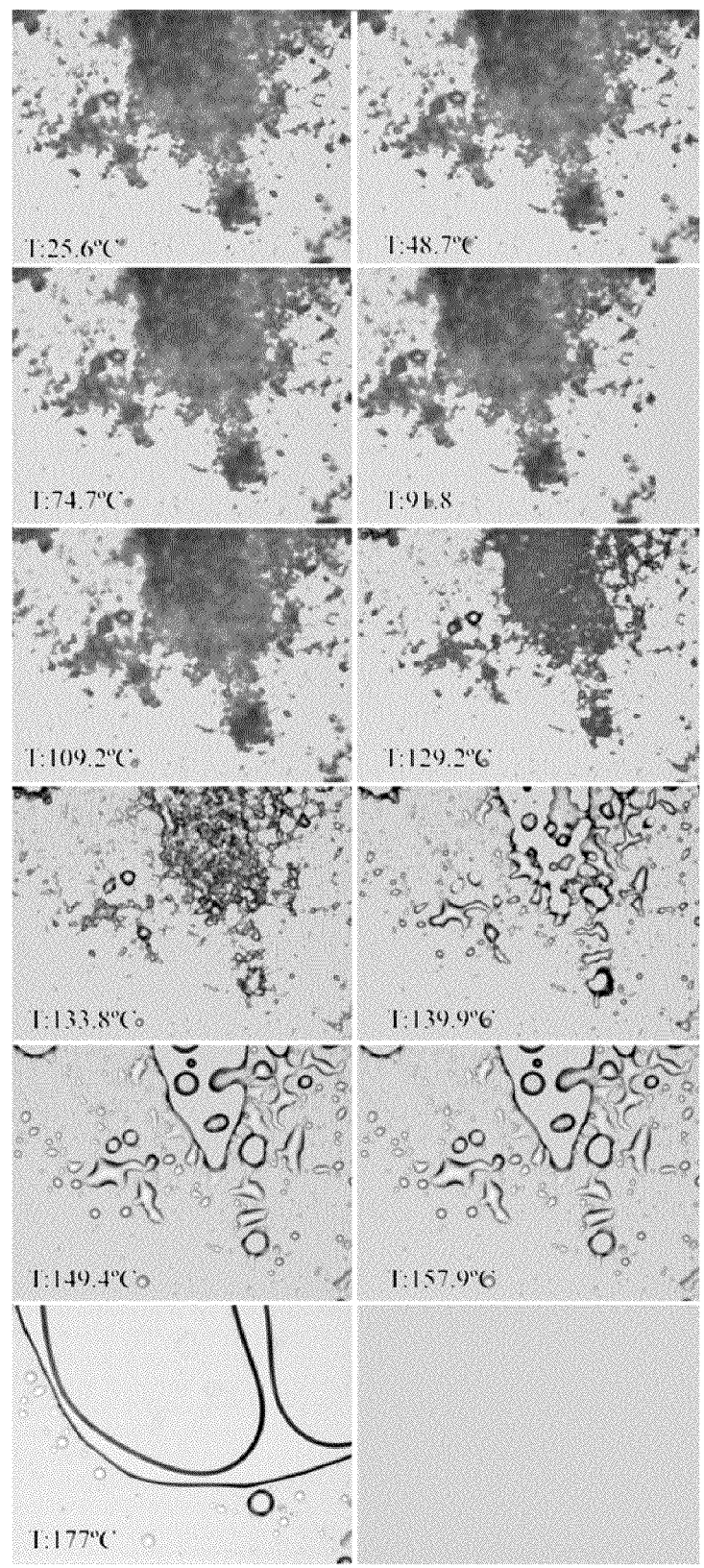
FIG. 14 illustrates the hostage microscopy photomicrographs of amorphous SEQ ID NO:1 (112409). Reference temperatures are provided for each micrograph.

Hot-stage microscopy (HSM) photomicrographs for lot A1922-001 are shown in FIG. 14. No significant change is

TABLE III

Supplemental data from Dynamic Vapor Sorption (DVS) analysis of SEQ ID NO: 1.

| Step Time min | Elap Time min | Weight mg | Weight % chg | Samp Temp deg C. | Samp RH % | Corr. % Wt. Chg. (mg) |
|---|---|---|---|---|---|---|
| n/a | 0.1 | 6.428 | 0.000 | 24.76 | 4.27 | n/a |
| 57.7 | 57.8 | 6.345 | −1.294 | 24.75 | 5.18 | 0.0000 |
| 26.1 | 83.9 | 6.385 | −0.674 | 24.75 | 15.11 | 0.6197 |
| 21.4 | 105.3 | 6.415 | −0.208 | 24.75 | 25.05 | 1.0859 |
| 25.0 | 130.3 | 6.445 | 0.257 | 24.75 | 34.99 | 1.5510 |
| 28.5 | 158.8 | 6.478 | 0.774 | 24.75 | 44.99 | 2.0675 |
| 38.3 | 197.1 | 6.521 | 1.446 | 24.74 | 54.87 | 2.7395 |
| 33.9 | 231.0 | 6.629 | 3.131 | 24.75 | 64.87 | 4.4243 |
| 39.8 | 270.8 | 6.769 | 5.310 | 24.74 | 74.84 | 6.6038 |
| 183.8 | 454.6 | 7.019 | 9.192 | 24.75 | 84.86 | 10.4855 |
| 183.6 | 638.2 | 7.953 | 23.731 | 24.74 | 94.84 | 25.0244 |
| 183.5 | 821.7 | 7.148 | 11.200 | 24.73 | 85.11 | 12.4939 |
| 183.6 | 1005.3 | 6.864 | 6.781 | 24.73 | 75.05 | 8.0745 |
| 186.0 | 1191.3 | 6.719 | 4.530 | 24.72 | 64.85 | 5.8234 |
| 185.9 | 1377.2 | 6.633 | 3.181 | 24.73 | 54.98 | 4.4746 |
| 186.0 | 1563.2 | 6.575 | 2.280 | 24.73 | 45.15 | 3.5736 |
| 173.6 | 1736.8 | 6.529 | 1.570 | 24.73 | 35.16 | 2.8640 |
| 183.9 | 1920.7 | 6.363 | −1.011 | 24.74 | 25.11 | 0.2823 |
| 182.6 | 2103.3 | 6.275 | −2.384 | 24.75 | 15.05 | −1.0898 |
| 183.0 | 2286.3 | 6.142 | −4.447 | 24.76 | 5.10 | −3.1536 |

Maximum equilibration time was 180 min. Quil critical was 0.0100 wt % in 5.00 min. RH steps were 25, 5; 25, 15; 25, 25; 25, 35; 25, 45; 25, 55; 25, 65; 25, 75; 25, 85; 25, 95; 25, 85; 25, 75; 25, 65; 25, 55; 25, 45; 25, 35; 25, 25; 25, 15; 25, 5.
−1.2938% wt change upon equilibration at 5% RH
25.0244% wt gain from 5%-95% RH
28.1780% wt lost from 95%-5% RH observed in the material from ambient temperature up to ~109.2° C. At ~129.2° C., the onset of liquefaction is observed and is completed at about 134° C. Above this temperature, the material is a liquid and shows evidence of discoloration at ~177° C., which is consistent with the onset of decomposition observed by DSC and TG.

Example 12

Fast Evaporation (FE)

Solutions were prepared in various solvents at ambient temperature and passed through a 0.2-μm nylon filter into a glass vial. The filtered solution was allowed to evaporate at ambient in an uncapped vial. Solids were isolated.

Example 13

Slow Evaporation (SE)

Solutions were prepared in various solvents at ambient temperature and passed through a 0.2-μm nylon filter into a glass vial. The filtered solution was allowed to evaporate at ambient in a vial covered with aluminum foil perforated with one or more pinholes. Solids were isolated.

In another aspect, the present invention provides a process for preparing amorphous form of SEQ ID NO: 1 comprising the steps of preparing a solution of SEQ ID NO:1 in a solvent. Examples of such solvents include water, methanol, ethanol, 2-propanol, 2-butanone, ethyl acetate, dichloromethane, tetrahydrofuran, 1-butanol, acetone, acetonitrile, ethyl acetate, chloroform, toluene, hexane, water:toluene, water:toluene:chloroform, chloroform:methanol, toluene:methanol, isopropyl ether, pentane:ethanol, heptane:ethanol, toluene:methanol, and a mixture thereof, and recovering the precipitated amorphous by slow or fast evaporation. The thermal data are summarized in Table IV.

TABLE IV

Characterization of SEQ ID NO: 1

| Analysis | Results (d) |
| --- | --- |
| XRPD | x-ray amorphous |
| TGA | 4.5 w % (T < 125° C.) |
|  | 201.5 (onset, decomp) |
|  | 35.6 w % (T > 201.5° C.) |
| DSC (b) | 51.1° C. (onset, endo) |
|  | 57.5° C. (peak, endo) |
|  | 92.8° C. (peak, endo) |
|  | 148.8° C. (peak, endo) |
|  | 218.3° C. (peak, endo) |
| DSC (c) | 69.2° C. (onset, endo, step_1) |
|  | 71.6° C. (peak, endo, step_1) |
|  | 58.0° C. (onset, endo, step_1) |
|  | 150.9° C. (peak, endo, step_3) |
|  | 222.9° C. (peak, endo, step_3) |
| mDSC | 67.2° C. (peak, endo, rev) |
| DVS | 5%-95% RH; 25.0 w % (gain), |
|  | 95%-5% RH; 28.2 w % (loss) |
| HSM | liquefaction at ~134° C. |

DSC (b): single heating step from −50 to 350° C.;
DSC (c): performed after ~63 days with temperature cycling;
(i) heat to 110° C.,
(ii) cool to −50° C., and
(iii) heat to 350° C.

In another aspect, the present invention provides a process for preparing amorphous form of SEQ ID NO:1 comprising the steps of preparing a solution of SEQ ID NO:1 in a solvent such as water, methanol, ethanol, trifluoroethanol, pentane:methanol, and toluene:water, and precipitating SEQ ID NO:1 with an antisolvent such as dichloromethane, toluene, heptane, acetonitrile, isopropyl ether, ethyl acetate, chloroform, pentane, tetrahydrofuran, acetone, 2-propanol, and a mixture thereof, to obtain SEQ ID NO:1 and recovering the amorphous SEQ ID NO:1. Summary of these experiments are in Table V.

TABLE V

Vapor diffusion of SEQ ID NO: 1.

| Solvent | Antisolvent | Habit/Description |
| --- | --- | --- |
| Water | DCM | x-ray amorphous |
|  | Toluene | no solids (a) |
| Water | Heptane | solids (a) |
| Water | ACN | amorphous |
|  | IPE | loose agglomerates (b) |
| Water | EtOAc | amorphous |
|  | Chloroform | no solids |
| MeOH | DCM | amorphous |
|  | Chloroform | glassy solids |
| MeOH | Heptane | no solids |
| MeOH | ACN | amorphous |
|  | Toluene | glassy solids (c) |
| MeOH | EtOAc | amorphous |
|  | Pentane | off-white solids (c) |
| EtOH | DCM | — |
|  | Pentane | glassy solids (c) |
| EtOH | Heptane | solids (a) |
| EtOH | ACN | amorphous |
|  | Chloroform | glassy solids (c) |
| EtOH | EtOAc | amorphous |
|  | IPE | white solids (c) |
| MeOH | THF | amorphous |
|  | Pentane | glassy solids (c) |
| MeOH | Toluene | solids (a) |
|  | Acetone | solids (a) |
| TFE | DCM | loose agglomerates |
|  | Toluene | no solids |
| TFE | 2-Propanol | amorphous |
|  | Chloroform | glassy solids (c) |
| Pentane:MeOH (2:1) | Heptane | loose agglomerates (b) |
|  | EtOAc | no solids |
| Toluene:Water (2:1) | Heptane | no solids (b) |
| Toluene:Water (2:1) | EtOAc | amorphous |
|  | IPE | glassy solids (c) |
|  | Chloroform | thin film (c) |

Heating at 50° C. and slow evaporation at ambient temperature
(a); slow evaporation at ~4° C.
(b); stored at 70° C.
(c). The ratio of different solvents volumes is in ml.

In another aspect, the present invention provides a process for preparing amorphous form of SEQ ID NO:1 comprising the steps of heating a solution of SEQ ID NO:1 in a solvent such as, by way of example only, ethanol, 2-propanol, ethyl acetate, dichloromethane to obtain amorphous SEQ ID NO:1 and recovering the amorphous SEQ ID NO:1.

In another aspect, the present invention provides a process for preparing amorphous form of SEQ ID NO:1 comprising the steps of cooling a solution of SEQ ID NO:1 in a solvent such as water, toluene, hexane, chloroform, ethyl acetate ethanol to obtain amorphous SEQ ID NO:1 and recovering the amorphous SEQ ID NO:1.

In another aspect, the present invention provides a process for preparing amorphous form of SEQ ID NO:1 comprising the steps of acidifying a solvent such as acetonitrile and acetonitrile:water and slow cooling to obtain amorphous SEQ ID NO:1 and recovering the amorphous SEQ ID NO:1 (Table VI).

TABLE VI

Salts of SEQ ID NO: 1.

| Solvent/Acid | Condition | Habit/Description |
|---|---|---|
| ACN/HCl (1:1) (c) | SC (60° C.)/SE | off-white (a) |
| ACN:Water (1:0.2) (e) H$_2$SO$_4$ (1:1) (d) | SC (60° C.)/SE | glassy solids (b) |

SEQ ID NO: 1 was stored at 70° C., followed by storage at 40° C./75% RH and vacuum dried (a); stored at 70° C.
(b); 1N hydrochloric acid added to solution to achieve 1:1 molar ratio of acid to SEQ ID NO: 1
(c);: 2.5 M sulfuric acid added to solution to achieve 1:1 molar ratio of acid to SEQ ID NO: 1
(d). ): The ratio of solvent volume is in ml.

In another aspect, the present invention provides a process for preparing amorphous form of SEQ ID NO:1 comprising the steps of acidifying a suspension of SEQ ID NO:1 in methanol, wherein the acidifying was at a molar ratio of 1:1 or 2:1 to obtain amorphous SEQ ID NO:1 and recovering the amorphous SEQ ID NO:1 Table VII).

TABLE VII

Salts of SEQ ID NO: 1 in immiscible solvents.

| Solvent/Acid | Antisolvent | Habit/Description |
|---|---|---|
| MeOH/HCl (1:1) (c) | Hexane | white solids (a) glassy solids (b) |
| MeOH/HCl (2:1) (c) | Hexane | white solids (a) glassy solids (b) |

SEQ ID NO: 1 was stored at 70° C. followed by storage at 40° C./75% RH and vacuum dried (a); stored at 70° C.
(b); 1N hydrochloric acid added to solution to achieve 1:1 molar ratio of acid to SEQ ID NO: 1
(c);: 2.5 M sulfuric acid added to solution to achieve 1:1 molar ratio of acid to SEQ ID NO: 1
(d). ): The ratio of solvent volume is in ml. The bottom and top layers retained for slow evaporation at ambient temperature.

In another aspect, the present invention provides a process for preparing amorphous form of SEQ ID NO:1 comprising the steps of acidifying a suspension of SEQ ID NO:1 in methanol, wherein the acidifying was at a molar ratio of 1:1 or 2:1 to obtain amorphous SEQ ID NO:1 and recovering the amorphous SEQ ID NO:1 (Table VIII).

TABLE VIII

Salts of SEQ ID NO: 1.

| Solvent (a) | Conditions | Habit/Description | XRPD Result |
|---|---|---|---|
| Water:Toluene (1:2) | FE | dry film | x-ray amorph + peaks |
| Water:Toluene (1:(a) | | dry film | x-ray amorph + peaks |
| Water:Toluene:EtOAc (1:2:0.1 (a) | | dry film | x-ray amorph + peaks |
| Water:Toluene (1:2) | | dry film | x-ray amorph + peaks |
| Water:Toluene (1:2)(a) | | dry film | x-ray amorph + peaks |
| Water:Toluene:Chloroform (1:2:0.2)(a) | | dry film | x-ray amorph + peaks |
| Water | SC/FE (c) | dry film | x-ray amorph + peaks |
| Toluene | | dry film | x-ray amorph + peaks |

TABLE VIII-continued

Salts of SEQ ID NO: 1.

| Solvent (a) | Conditions | Habit/Description | XRPD Result |
|---|---|---|---|
| Hexane | | dry film | x-ray amorph |
| Chloroform | | dry film | x-ray amorph |
| Ethyl Acetate (EtOAc) | | dry film | x-ray amorph |

1N hydrochloric acid added to solution to achieve 2:1 molar ratio (a) or 1:1 molar ratio (B) of acid to SEQ ID NO: 1. The ratio of solvent volumes in ml provided in parentheses.
FE: fast evaporation (ambient temperature);
SC: slow cooled (from ~60° C. to ambient temperature).

Example 14

Vapor Diffusion (VD)

Solutions were prepared with various solvents at ambient temperature and passed through a 0.2 μm nylon filter into a glass vial. This filled vial was placed in a glass vial containing an anti-solvent and capped. In general, the anti-solvent is miscible with and, typically, more volatile than the solvent. The experiment was left undisturbed at ambient temperature. Solids were isolated.

Example 15

Temperature Cycling (TC)

Solutions prepared for experiment were capped in a glass vial and cycled between different temperatures.

Example 16

Salt Precipitation

SEQ ID NO:1, along with selected counter-ions were added to a glass vial. Specific solvents were then transferred to the glass vial and the solution passed through a 0.2 μm nylon filter; in some cases, counter-ions were added after solvent addition. The filtered solution was allowed to evaporate at ambient in a vial covered with aluminum foil perforated with one or more pinholes. Solids were isolated.

Example 17

Immiscible Solvent/Anti-Solvent Precipitation

SEQ ID NO:1, along with selected counter-ions were added to a glass vial. Specific solvents were then added to the glass vial and the solution and passed through a 0.2-μm nylon filter. Specific anti-solvents were then added to the glass vial. In general, the anti-solvent was immiscible with the solvent. The solution was allowed to mix and then the two solvent layers were separated into separate glass vials using a pipette. The solutions were allowed to evaporate at ambient temperature covered with aluminum foil perforated with one or more pinholes. Solids were isolated.

The examples and embodiments described herein are for illustrative purposes only and various modifications or changes suggested to persons skilled in the art are to be included within the spirit and purview of this application and scope of the appended claims. All publications, patents, and patent applications cited herein are hereby incorporated by reference for all purposes.

What is claimed is:

1. A crystal of a peptide consisting of SEQ ID NO: 1, wherein said crystal comprises an asymmetric unit, said asymmetric unit comprises 4 molecules of said peptide per $Zn^{2+}$ and further wherein the crystal belongs to space group $P2_1$ or $P2_12_12$.

2. A crystal of a peptide consisting of SEQ ID NO: 1, wherein said crystal comprises an asymmetric unit, said asymmetric unit comprises 2 molecules of said peptide per $Zn^{2+}$ and further wherein the crystal belongs to space group $P2_1$ or $P2_12_12$.

* * * * *

```
                          SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Leu Pro Ser
1
```